US010087285B2

(12) United States Patent
Bolikal et al.

(10) Patent No.: US 10,087,285 B2
(45) Date of Patent: Oct. 2, 2018

(54) BIOCOMPATIBLE IODINATED DIPHENOL MONOMERS AND POLYMERS

(71) Applicant: Rutgers, The State University of New Jersey, New Brunswick, NJ (US)

(72) Inventors: Durgadas Bolikal, Edison, NJ (US); Joachim B. Kohn, Piscataway, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 290 days.

(21) Appl. No.: 14/983,801

(22) Filed: Dec. 30, 2015

(65) Prior Publication Data
US 2016/0177028 A1 Jun. 23, 2016

Related U.S. Application Data

(63) Continuation of application No. PCT/IB2015/059967, filed on Dec. 23, 2015.

(60) Provisional application No. 62/096,420, filed on Dec. 23, 2014, provisional application No. 62/138,572, filed on Mar. 26, 2015.

(51) Int. Cl.
| A61K 49/04 | (2006.01) |
| C08G 64/10 | (2006.01) |
| C08G 81/00 | (2006.01) |
| C08G 63/64 | (2006.01) |
| C07C 69/84 | (2006.01) |

(52) U.S. Cl.
CPC .......... *C08G 64/10* (2013.01); *A61K 49/0442* (2013.01); *C07C 69/84* (2013.01); *C08G 63/64* (2013.01); *C08G 81/00* (2013.01)

(58) Field of Classification Search
CPC ........ C08G 64/10; C08G 63/64; C08G 81/00; C07C 69/84; C07D 403/06; A61K 49/0442
See application file for complete search history.

(56) References Cited

U.S. PATENT DOCUMENTS

| 3,636,956 A | 1/1972 | Schneider |
| 3,663,515 A | 5/1972 | Hostettler et al. |
| 4,043,981 A * | 8/1977 | O'Brien ............. C08G 63/6822 525/437 |
| 4,162,314 A | 7/1979 | Gottschlich et al. |
| 4,230,817 A | 10/1980 | Charbonneau |
| 4,331,782 A | 5/1982 | Linden |
| 4,744,365 A | 5/1988 | Kaplan et al. |
| 4,747,956 A | 5/1988 | Kiniwa |
| 4,822,829 A | 4/1989 | Muller et al. |
| 4,980,449 A | 12/1990 | Kohn et al. |
| 5,003,004 A | 3/1991 | Simms |
| 5,066,772 A | 11/1991 | Tang et al. |
| 5,082,925 A * | 1/1992 | Shalaby ................. A61L 31/06 528/354 |
| 5,099,060 A | 3/1992 | Kohn et al. |
| 5,216,115 A | 6/1993 | Kohn et al. |
| 5,219,564 A | 6/1993 | Zalipsky et al. |
| 5,403,347 A | 4/1995 | Roby et al. |
| 5,431,679 A | 7/1995 | Bennett et al. |
| 5,587,507 A | 12/1996 | Kohn et al. |
| 5,660,822 A | 8/1997 | Poiani et al. |
| 5,665,831 A | 9/1997 | Neuenschwander et al. |
| 5,670,602 A | 9/1997 | Kohn et al. |
| 5,702,717 A | 12/1997 | Cha et al. |
| 5,854,383 A | 12/1998 | Emeta et al. |
| 5,916,998 A | 6/1999 | Ferruti et al. |
| 5,952,450 A | 9/1999 | Ishihara et al. |
| 6,120,491 A | 9/2000 | Kohn et al. |
| 6,150,491 A | 11/2000 | Akkara |
| 6,228,969 B1 | 5/2001 | Lee et al. |
| 6,316,585 B1 | 11/2001 | Lele et al. |
| 6,355,754 B1 | 3/2002 | Olson et al. |
| 6,475,477 B1 | 11/2002 | Kohn et al. |
| 6,592,899 B2 | 7/2003 | Fowers et al. |
| 6,602,497 B1 | 8/2003 | Kohn et al. |
| 6,943,214 B2 | 9/2005 | Flexman |
| 7,166,134 B2 | 1/2007 | Datta et al. |
| 7,169,187 B2 | 1/2007 | Datta et al. |
| 7,479,157 B2 | 1/2009 | Weber et al. |
| 8,252,877 B2 | 8/2012 | Hirano et al. |
| 8,476,399 B2 | 7/2013 | Bolikal et al. |
| 8,551,511 B2 | 10/2013 | Brandom et al. |

(Continued)

FOREIGN PATENT DOCUMENTS

| CA | 2412161 A1 | 12/2001 |
| CA | 2412718 A1 | 1/2002 |

(Continued)

OTHER PUBLICATIONS

Plage et al. "Thermal Degradation and Mass Spectrometric Fragmentation Processes of Polyesters Studied by Time/Temperature Resolved Pyrolysis Field Ionization Mass Spectroscopy", Macromolecules, 23, 2642-2648, 1990. (Year: 1990).*
Imasaka et al. Synthesis and in vitro degradation of low molecular weight copolyesters composed of L-lactic acid and aromoatic hydroxy acids) Makromolekular Chemie, 191, 2077-2082, 1990. (Year: 1990).*
Hermann, K. et al., Photoreactive Polyanhydrides Containing Cinnamic Acid Units in the Main Chain, Macromolecular Reports, A31(Suppls. 6&7, 1279-1283 (1994).
Caracciolo, P.C. et al., Effect of the hard segment chemistry and structure on the thermal and mechanical properties of novel biomedical segmented poly(esterurethanes), J. Mater Sci: Mater Med (2009) 20:145-155.
XP-002762099, Database WPI, Week 199602, Thomson Scientific, 1996 (2 pages).

(Continued)

Primary Examiner — Christopher M Rodd
(74) Attorney, Agent, or Firm — Fox Rothschild LLP

(57) ABSTRACT

Disclosed are monomeric compounds which may be polymerized to form novel biodegradable and bioresorbable polymers and co-polymers. These polymers and co-polymers, while not limited thereto, may be adapted for radiopacity and are useful for medical device applications and controlled release therapeutic formulations.

81 Claims, No Drawings

(56) References Cited

U.S. PATENT DOCUMENTS

| | | |
|---|---|---|
| 2001/0046505 A1 | 11/2001 | Kohn et al. |
| 2003/0068384 A1 | 4/2003 | Brocchini et al. |
| 2004/0082734 A1 | 4/2004 | Hatton et al. |
| 2005/0106119 A1 | 5/2005 | Brandom et al. |
| 2006/0024266 A1 | 2/2006 | Brandom et al. |
| 2006/0034769 A1 | 2/2006 | Kohn et al. |
| 2006/0034891 A1 | 2/2006 | Lawin et al. |
| 2006/0036316 A1 | 2/2006 | Zeltinger et al. |
| 2006/0178477 A1 | 8/2006 | Neuenschwander |
| 2007/0117959 A1 | 5/2007 | Shastri et al. |
| 2007/0135355 A1 | 6/2007 | Bezwada |
| 2007/0190151 A1 | 8/2007 | Chai et al. |
| 2007/0231365 A1 | 10/2007 | Wang et al. |
| 2007/0282435 A1 | 12/2007 | Wang et al. |
| 2008/0063685 A1 | 3/2008 | Wang et al. |
| 2008/0112999 A1 | 5/2008 | Baluca |
| 2008/0146504 A1 | 6/2008 | Bonnin |
| 2008/0152690 A1 | 6/2008 | Kohn et al. |
| 2008/0187567 A1 | 8/2008 | Kohn et al. |
| 2008/0221295 A1* | 9/2008 | Ishikawa ............ C08G 63/64 528/176 |
| 2008/0243049 A1 | 10/2008 | Hardy |
| 2008/0243228 A1 | 10/2008 | Wang et al. |
| 2008/0269874 A1 | 10/2008 | Wang et al. |
| 2009/0004243 A1 | 1/2009 | Pacetti et al. |
| 2009/0035350 A1 | 2/2009 | Stankus et al. |
| 2009/0088835 A1 | 4/2009 | Wang |
| 2010/0234555 A1 | 9/2010 | Bolikal et al. |
| 2013/0203713 A1 | 8/2013 | Kohn et al. |
| 2015/0045451 A1 | 2/2015 | Bolikal et al. |

FOREIGN PATENT DOCUMENTS

| | | |
|---|---|---|
| JP | H0618946 A | 1/1994 |
| JP | H07292084 A | 11/1995 |
| JP | H07295221 A | 11/1995 |
| JP | H1513985 A | 11/1999 |
| JP | 2004-513971 | 5/2004 |
| JP | 2007-506791 | 3/2007 |
| JP | 2008506019 A | 2/2008 |
| JP | 2008-509722 | 4/2008 |
| JP | 2008-510034 | 4/2008 |
| JP | 2009503187 A | 1/2009 |
| WO | 1989/001005 A1 | 2/1989 |
| WO | 91/06569 A1 | 5/1991 |
| WO | 9715287 A1 | 5/1997 |
| WO | 1997/019996 | 6/1997 |
| WO | 1998/036013 A1 | 8/1998 |
| WO | 1999/024391 | 5/1999 |
| WO | 2005/030268 A1 | 4/2005 |
| WO | 2006/022754 A2 | 3/2006 |
| WO | 2006/060235 A2 | 6/2006 |
| WO | 2007/018544 A2 | 2/2007 |
| WO | 2007047244 A2 | 4/2007 |
| WO | 2007/050583 A2 | 5/2007 |
| WO | 2007/056134 | 5/2007 |
| WO | 2007/143698 | 12/2007 |
| WO | 2008/082738 A2 | 7/2008 |
| WO | 2008105652 A1 | 9/2008 |
| WO | 2010/033640 | 3/2010 |
| WO | 2010/042917 | 4/2010 |
| WO | 2015/126666 A1 | 8/2015 |

OTHER PUBLICATIONS

XP-002762086, Database Caplus, Chemical Abstracts Service, Feb. 1, 1995 (3 pages).
Extended European Search Report dated Nov. 3, 2016 issued in European Patent Application No. 09820026.4 (22 pages).
International Search Report and Written Opinion of the Searching Authority dated Sep. 7, 2016 for International Application No. PCT/US16/35723 (14 pages).
International Search Report and Written Opinion of the International Searching Authority dated May 2, 2016, for Application No. PCT/162015/059967.
International Search Report and Written Opinion dated Dec. 3, 2009 for International Application No. PCT/US09/60301.
Dobrzynski et al. Structure-Property Relationships of Copolymers Obtained by Ring-Opening Polymerization of Glycolide and e-Caprolactone. Part 1. Synthesis and Characterization. Biomacromolecules 6(1): 483-488. 2005.
Green and Wuts, "Protective Groups in Organic Synthesis" 3rd Ed. John Wiley & Sons, New York, NY, 1999 (Abstract Only).
Laurencin et al. "Poly(anhydride) administration in high doses in vivo: studies of biocompatibility and toxicology", J. Biomed. Mat Res.; 1463-1481, 1990 (Abstract only).
Mligiliche et al., ",Poly lactic acid-caprolactone copolymer tube with a denatured skeletal muscle segment inside as a guide for peripheral nerve regeneration: A morphological and electrophysiological evaluation of the regenerated nerves,"Anatamical Science International, vol. 78, No. 3, Sep. 2003, pp. 156-161. (Abstract).
Nathan et al., "Copolymers of Lysine and Polyethylene Glycol: A New Family" Bio. Cong. Chem., (1993) vol. 4, pp. 54-62.
Nathan et al., "Hydrogels Based on Water-Soluble Poly(ether urethanes) Derived from L-Lysine and Poly(ethylene glycol)" Macromol., (1992) vol. 25, pp. 4476-4484.
Plate et al., "Comb-like polymers. Structure and properties." J. Polymer Sci., Macromol. Rev. vol. 8, pp. 117-253 (1974) (Abstract only).
Polycarprolactone diol, 2011 obtained from the Sigma-Aldrich website: (http://www.sigmaaldrich.com/catalog/productDetail.do?D7=0&N5=SEARCH.sub.- —CONCAT.sub.--PNO%7CBRAND.sub.--KEY&N4=189421% 7CALDRICH&N25=0&QS=ON&F= SPE- C).
Sousa, A., et al., "Selective Protein Adsorption on a Phase-Separated Solvent-Cast Polymer Blend", Langmuir, 22, 2006, pp. 6286-6292.
Tangpasuthadol, V., et al., "Thermal properties and physical ageing behaviour of tyrosine-derived polycarbonates", Biomaterials, 1996, vol. 17, No. 4., pp. 463-468.
Teng et al., "Synthesis and characterization of poly(L-lactic acid)-poly(e-caprolactone) multiblock copolymers by melt polycondensation," Journal of Polymer Science Part A: Polymer Chemistry. 42: pp. 5045-5053, 2004. (Abstract).
Kaneko et al., "Environmentally degradable, high-performance thermoplastics from phenolic phytomonomers", Nature Materials, vol. 5, pp. 966-970 (2006).
Kaneko, "High-Performance Functional Ecopolymers Based on Flora and Fauna", Chemical Record vol. 7(4), pp. 210-219 (2007).
Mosher et al., "Polypeptides from r-Phenylalanine Mustard", J. Met Chem. vol. 7(5), pp. 650-652 (1964).
Schmaljohann et al., Conversion dependence of the structural units and the degree of branching of a hyperbranched polyester based on 4,4-bis-(4'-hydroxyphenyl)pentanoic acid determined by NMR spectroscopy, Acta Polym. vol. 50, pp. 196-204 (1999).
Mikroyannidis, "Synthesis, properties and crosslinking of unsaturated cyano-substituted homo- and copolyesters prepared from 1-hydroxy-4-(2-cyano-2-carboxyvinyl)benzene", Polymer vol. 36(6), pp. 1287-1293 (1995).
Fuso et al., "Poly[(w-hydroxyalkyl)thio-a-cyanocinnamates]. Linear Polyesters with NLO-Phores in the Main Chain", Macromolecules vol. 24, pp. 1710-1713 (1991).
Ten Brink et al: "Synthesis of Alkyne-Bridged Cyclic Tripeptides Toward Constrained Mimics of Vancomycin", Journal of Organic Chemistry, 2006, vol. 71, No. 5, pp. 1817-1824.
Shiotani, et al: "Studies on Diazabenzobicyclo[3.3.1]noname System. VIII.1) Synthesis of 8,9-Dimethoxy-11-benzoyl-1,2,5,6-tetrahydro-2,6-imino-3-benzazocin-4(3-H)-one", Chem. Pharm. Bull, 1968, vol. 16, No. 2, pp. 239-245.
Berse, et al: "The Preparation of Succinamido Peptides", Journal of Organic Chemistry, Published 1962, vol. 27, pp. 3489-3495.
6-(4-Carboxy-1,4-Dioxobutoxy)Tryptophan, Compound w2ith 5-Hydroxy-6-Methylpyridine-3,4-Dimethanol (1:1), Chemical Book, Retrieved from the Internet<URL: http://www.chemicalbook.com/ChemicalProductProperty_CN_CB1896543.htm>.

(56) References Cited

OTHER PUBLICATIONS

Latham, K. et al., "Development of Support Matrices for Affinity Chromatography of Thyroid Hormone Receptors," The J. of Biological Chem, Dec. 10, 1981, vol. 256, pp. 12088-12093.

Perez, P. et al., "Bioresorbable and Nonresorbable Macroporous Thermosensitive Hydrogels Prepared by Cryopolymerization. Role of the Cross-Linking Agent," Biomacromolecules 2008, vol. 9, pp. 66-74.

Tang, S. et al., "Synthesis and Characterization of Water-Soluble and Photostable L-Dopa Dendrimers," Organic Letters, 2006, vol. 8, No. 20, pp. 4421-4424.

Ross, et al.; "Carbon Suboxide and Proteins, III. The Reaction of Carbon Suboxide with Amino Acids"; Journal of Biological Chemistry, 1941, vol. 37, pp. 105-111.

Zhang et al.: "Synthesis and Biological Activities of QuinazolineDerivatives with Ortho-Phenol_Quaternary Ammonium Salt Groups", Bioorganic & Medicinal Chemistry, 2007, vol. 15, Issue 22, pp. 6920-6926.

Ross, et al.: "Carbon Suboxide and Proteins"; Journal of Biological Chemistry, Published 1941, vol. 37, pp. 105-111.

Imasaka et al: "New Biodegradable Polymers of L-lactic Acid and Aromatic Hydroxy Acids and Their Applications in Drug Delivery Systems", International Journal of Pharmaceutics, 1992, vol. 81, pp. 31-38.

Jin, et al: "Synthesis, Characterization, and In Vitro Degradation of a Novel Thermotropic Ternary Copolyester Based on p-Hydroxybenzoic Acid, Glycolic Acid, and p-Hydroxycinnamic Acid", Macromolecules, Jul. 3, 1995, vol. 28, No. 14, pp. 4785-4794.

Nagata, et al: "Biodegradable Elastic Photocured Polyesters Based on Adipic Acid, 4-hydroxycinnamic Acid and Poly (e-caprolactone) diols", Polymer, 2004, vol. 45, pp. 87-93.

Du, et al: "Synthesis, Characterization and Biodegradation of Biodegradable-cum-photoactive Liquid-Crystalline Copolyesters Derived From Ferulic Acid", Polymer, 2007, vol. 48, pp. 5541-5547.

Beaulieu, et al: "Non-Nucleoside Inhibitors of the Hepatitis C Virus NS5B Polymerase: Discovery of Benzimidazole 5-Carboxylic Amid Derivatives with Low-Nanomolar Potency", Bioorganic & Medicinal Chemistry Letters, 2004, vol. 14 pp. 967-971.

Cascales, et al: "Tiratricol Neutralizes Bacterial Endotoxins and Reduces Lipopolysaccharide-Induced TNF-x Production in the Cell", Chem Biol Drug Des, 2008, vol. 72, pp. 320-328.

Majeska, et al: "Effects of Plate Preparation on Results in Microbial Mutation Assays", Environmental and Molecular Mutagenesis, 1992, vol. 19, pp. 244-252.

Covello, et al: "Synthesis and Properties of 2-Hydroxy-And 2-Acetoxy-5-Iodobenzoic Acid Polyesters of Short-Chain Aliphatic Polyalcohols", Oct. 1, 1968, La Ricerca Scientifica, vol. 38, No. 10, pp. 933-936.

\* cited by examiner

BIOCOMPATIBLE IODINATED DIPHENOL MONOMERS AND POLYMERS

CROSS-REFERENCE TO RELATED APPLICATIONS

This application is a continuation of PCT/IB2015/059967, filed Dec. 23, 2015, which claims priority under 35 U.S.C. § 119(e) to U.S. Provisional Patent Applications No. 62/138,572 filed on Mar. 26, 2015 and 62/096,420 filed on Dec. 23, 2014, all of which are hereby incorporated by reference in their entirety for all purposes.

FIELD OF THE INVENTION

The present invention relates to new classes of monomeric compounds, which may be polymerized to form novel biodegradable and bioresorbable polymers and co-polymers. These polymers and co-polymers, while not limited thereto, may be adapted for radio-opacity and are useful for medical device applications and controlled release therapeutic formulations.

The present invention thus also relates to new biocompatible polymers suitable for use in implantable medical devices and monomers for such polymers. In particular, the present invention relates to polymers polymerized from monomer analogs of compounds that naturally occur in the human body and that contribute advantageous synthesis, processing and material properties to the polymers prepared therefrom.

BACKGROUND OF THE INVENTION

Diphenols are monomeric starting materials for polycarbonates, polyiminocarbonates, polyarylates, polyurethanes and the like. U.S. Pat. No. 5,099,060 discloses diphenolic monomers based on 3-(4-hydroxyphenyl) propionic acid and L-tyrosine alkyl esters (desaminotyrosyl-tyrosine alkyl esters). Subsequent related patents involve variations of this basic monomer structure, including halogenated radiopaque diphenolic monomers, such as the 3,5-diiododesaminotyrosyl-tyrosine esters (I2DTX, wherein X=ester group, e.g., E=ethyl, H=hexyl, O=octyl, etc.) disclosed by U.S. Patent Application Publication No. 2006/0034769. The disclosures of both publications are incorporated by reference. Examples of other polymers suitable for various bioengineering applications include those described in U.S. Pat. Nos. 5,665,831; and 6,475,477, along with the polymers described in U.S. Patent Publication No. 2006/0024266, the disclosures of all of which are also incorporated by reference.

U.S. Pat. Nos. 8,252,887 and 8,476,399 describe classes of monomeric compounds and biodegradable and bioresorbable polymers and co-polymers. The disclosures of each of these patents and application are also incorporated by reference.

Although these monomers are useful in the synthesis of polymers for many medical implant applications, the rapidly evolving field of bioengineering has created a demand for a diverse library of different types of polymers offering a wide variety of choice of physical and mechanical properties. It is desirable that libraries of many different materials be available so that the specific polymer properties can be optimally matched with the requirements of the specific applications under development.

BRIEF SUMMARY OF THE INVENTION

As set forth herein, the embodiments disclosed address these needs. Various embodiments provide polymer compositions derived from new monomers, medical devices containing such compositions, and methods of using such polymer compositions and devices.

New classes of monomeric compounds are provided, which may be polymerized to form novel polymers and co-polymers that, while not limited thereto, may be adapted for radio-opacity and are useful for medical device applications and controlled release therapeutic formulations, although not limited thereto. More specifically, the present invention introduces a novel class of monomers, which are polymerized to form polymers and copolymers with at least one or more aromatic repeating units that are analogs of compounds that naturally occur in the human body.

In one embodiment, copolymers are provided by reacting a hydroxyalkanoic acid or a sulfur or amino analog thereof having the structure of Formula Ia:

(1a)

with a hydroxyarylalkanoic acid or a hydroxyarylalkenoic acid or a sulfur or amino analog thereof having the structure of Formula Ib:

(1b)

wherein, $X_1$, $X_2$, $X_3$, $X_4$, $X_5$ and $X_6$ are independently selected from O, S and $NR_3$ wherein $R_3$ is selected from hydrogen and alkyl groups containing from one to six carbon atoms; $Ar_1$ is a phenylene group,

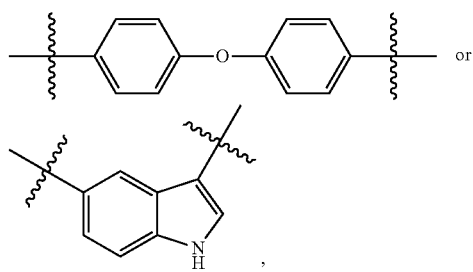

optionally substituted with from one to four substituents independently selected from a halogen, a halomethyl, a halomethoxy, a methyl, a methoxy, a thiomethyl, a nitro, a sulfoxide, and a sulfonyl; and B is selected from an optionally substituted alkylene group containing from 1 to 18 carbons, an optionally substituted heteroalkylene group containing from 1 to 18 carbon atoms, an optionally substituted alkenylene group containing from 2 to 18 carbon atoms and an optionally substituted heteroalkenylene group containing from 2 to 18 carbon atoms.

In one embodiment of Formula Ia, each of $X_1$, $X_2$, $X_3$, $X_4$ and $X_5$ are all oxygen atoms and $Ar_1$ is substituted with at least one halogen atom. While not limited thereto, in accordance with the above, a ring of $Ar_1$ may be substituted with two halogen atoms (e.g. iodine or bromine), preferably, in positions ortho to $X_1$. Furthermore, $R_1$ may be an alkyl group containing from one to ten carbon atoms, or may be a bond. In a preferred embodiment $R_1$ is a bond.

Embodiments are provided in which B is a methylene group, and $X_4$ and $X_5$ are oxygen, wherein the Formula Ia monomer is glycolic acid, and the resulting polymer is polyglycolic acid (PGA) copolymerized with the Formula Ib monomer.

Embodiments are also included in which B is a methyl-substituted methylene group and $X_4$ and $X_5$ are oxygen, wherein the Formula Ia monomer is lactic acid and the resulting polymer is polylactic acid (PLA) copolymerized with the Formula Ib monomer. Both glycolic acid and lactic acid may be used, in which case the resulting polymer is poly(lactic-co-glycolic acid) (PLGA) copolymerized with the Formula Ib monomer. When the Formula Ib monomer is radio-opaque, embodiments are provided that are radio-opaque analogs of PGA, PLA and PLGA.

In further embodiments, aromatic monomer compounds are provided having the structure of formula IIa:

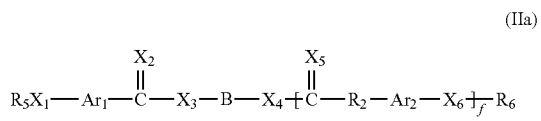
(IIa)

wherein f is 0 or 1, $X_1$, $X_2$, $X_3$, $X_4$, $X_5$ and $X_6$ are independently selected from O, S and $NR_3$ wherein $R_3$ is selected from hydrogen and an alkyl group containing from one to six carbon atoms. $Ar_1$ and $Ar_2$ is each independently a phenylene ring,

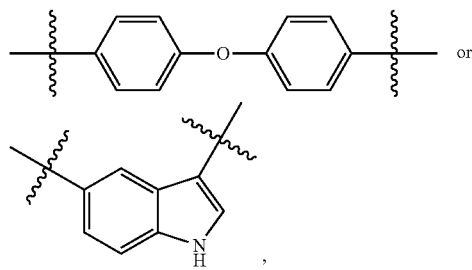

optionally substituted with from one to four substituents independently selected from halogen, halomethyl, halomethoxy, methyl, methoxy, thiomethyl, nitro, sulfoxide, and sulfonyl. $R_2$ is a bond or selected from optionally substituted alkyl, heteroalkyl, alkenyl and heteroalkenyl groups each containing from one to ten carbon atoms; $R_5$ and $R_6$ are independently selected from hydrogen and an alkyl group containing from one to six carbon atoms. B is selected from a carbonyl group, an optionally substituted alkyl group, an optionally substituted heteroalkyl group, an optionally substituted alkenyl group and an optionally substituted heteroalkenyl group, or B, $X_3$ and $X_4$ are selected so that $HX_3$—B—$X_4H$ defines a hydroxyl endcapped macromer, a mercapto endcapped macromer or an amine endcapped macromer.

Preferably B is selected from the group consisting of a carbonyl group, optionally substituted alkylene groups of 1 to 18 carbon atoms, and groups having the structure:

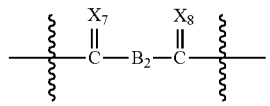

wherein $B_2$ is selected from the group consisting of optionally substituted alkylene, optionally substituted heteroalkylene, optionally substituted alkenylene and optionally substituted heteroalkenylene, or $B_2$, $X_3$, $X_4$, $X_7$ and $X_8$ are selected so that

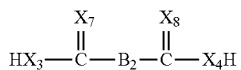

defines an endcapped macromer.

The compounds of Formula IIa are prepared by reacting one mole of a compound having the structure $HX_3$—B—$X_4H$ with either about one mole of the compound of Formula Ib (f=0) or about two moles of the compound of Formula Ib (f=1).

According to one embodiment, each of $X_1$, $X_2$, $X_3$, $X_4$, $X_5$, and $X_6$ is an oxygen atom. According to another embodiment, $Ar_1$ and $Ar_2$ are both independently substituted with at least one halogen atom.

In another embodiment both $Ar_1$ and $Ar_2$ are ortho-substituted with two iodine atoms. Furthermore, $R_2$ may be an alkyl group containing from one to ten carbon atoms, or may be a bond. In a preferred embodiment, $R_2$ is a bond. In further embodiments, B is a methylene group or a methyl-substituted methylene group.

In one embodiment, the hydroxy endcapped macromer block comprises at least one macromer block selected from a hydroxy endcapped polycaprolactone, a hydroxy endcapped polylactic acid, a hydroxy endcapped polyglycolic acid, a hydroxy endcapped poly(lactic acid-co-glycolic acid), a hydroxy endcapped poly(alkylene diol), a poly(alkylene oxide) and a hydroxy endcapped polydioxanone. In a further embodiment, the alkylene diol is hexane diol.

In one embodiment, the macromer dicarboxylate block comprises at least one macromer block selected from a polycaprolactone dicarboxylate, a polylactic acid dicarboxylate, a polyglycolic acid dicarboxylate, a poly(lactic acid-co-glycolic acid) dicarboxylate, a poly(alkylene diol) dicarboxylate, a poly(alkylene oxide) dicarboxylate and a polydioxanone dicarboxylate. In a further embodiment, the alkylene diol is hexane diol. The macromer block may be a homopolymer or the macromer block may be co-polymerized, for example, with phosgene, to form a carbonate macromer dicarboxylate.

When $R_5$ and $R_6$ of the Formula IIa compounds are alkyl, the compounds are not monomers but serve other potential end-uses where a non-reactive compound is desired, particularly when the compounds are radio-opaque.

Each of the foregoing compounds of Formula IIa may be adapted as a repeating unit in a polymeric composition having the structure of Formula IIb:

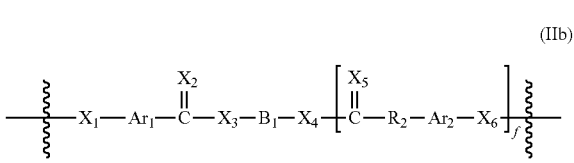
(IIb)

wherein f is 0 or 1, $X_1$, $X_2$, $X_3$, $X_4$, $X_5$, $X_6$, $X_7$, $X_8$, $R_2$, $R_3$, $R_5$, $R_6$, $Ar_1$, $Ar_2$, B, $B_1$ and $B_2$, and the preferred species thereof, are the same as described above with respect to Formula IIa.

Polymers according to Formula IIb include block copolymers with a hydroxy endcapped macromer, a mercapto endcapped macromer or an amino endcapped macromer. In one embodiment, the hydroxy endcapped macromer block comprises at least one macromer block selected from a hydroxy endcapped polycaprolactone, a hydroxy endcapped polylactic acid, a hydroxy endcapped polyglycolic acid, a hydroxy endcapped poly(lactic acid-co-glycolic acid), a hydroxy endcapped poly(alkylene diol), a poly(alkylene oxide) and a hydroxy endcapped polydioxanone. In a further embodiment, the alkylene diol is hexane diol. The macromer block may be a homopolymer or the macromer block may be copolymerized, for example with phosgene to form a hydroxy endcapped macromer carbonate.

While not limited thereto, macromer block copolymers of Formula IIb may have a molecular a weight ratio of polymer to hydroxy-capped macromer between about 25:75 and about 99:1.

The Formula IIb polymers also include polycarbonates, polyesters, polyphosphazines, polyphosphoesters and polyiminocarbonates. To this end, polymers having the structures of Formula IIb include polymers having the structure of Formula IIc:

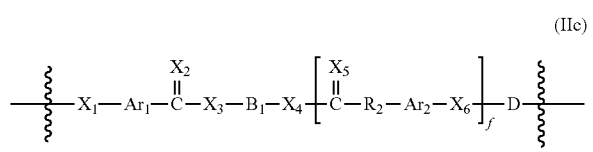

(IIc)

wherein D is selected from

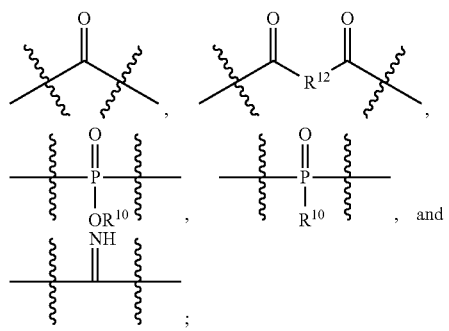

, and

;

wherein $R_{10}$ is selected from H, an optionally substituted alkyl group, an optionally substituted heteroalkyl group, an optionally substituted alkenyl group and an optionally substituted heteroalkenyl group, each optionally crystallizable and containing from one to 30 carbon atoms, and $R_{12}$ is selected from an optionally substituted alkyl group, an optionally substituted heteroalkyl group, an optionally substituted alkenyl group and an optionally substituted heteroalkenyl group, each containing from one to 18 carbon atoms and an optionally substituted alkylaryl group, an optionally substituted heteroalkylaryl group, an optionally substituted alkenylaryl group and optionally substituted heteroalkenylary group, each containing up to 12 carbon atoms.

D is additionally defined such that $HX_6$-D-$X_1H$ defines an alkylene diol containing up to 24 carbon atoms, an alkylene diamine containing up to 24 carbon atoms, an alkylene dimercaptan containing up to 24 carbon atoms; or a hydroxy endcapped macromer, a mercapto endcapped macromer or an amine endcapped macromer as previously defined.

In accordance with another embodiment, monomeric compounds of any of the foregoing may be polymerized so as to form a polymer or co-polymer with repeating units of any one or more of these monomers. After polymerization, appropriate work up of the polymers in accordance with preferred embodiments of the present invention may be achieved by any of a variety of known methods commonly employed in the field of synthetic polymers to produce a variety of useful articles with valuable physical and chemical properties, all derived from tissue compatible monomers. The useful articles can be shaped by conventional polymer thermoforming techniques such as extrusion and injection molding when the degradation temperature of the polymer is above the glass transition or crystalline melt temperature, or conventional non-thermal techniques can be used, such as compression molding, injection molding, solvent casting, spin casting, wet spinning. Combinations of two or more methods can be used. Shaped articles prepared from the polymers are useful, inter alia, as degradable biomaterials for medical implant applications.

In accordance with the discussion here, medical devices are provided comprising polymers disclosed herein, which are well-suited for use in producing a variety of resorbable medical devices or other implantable devices. Representative device embodiments include stents, disks, plugs, sutures, staples, clips, surgical adhesives, screws, anchors and the like. These and other similar implantable medical devices are preferably radiopaque, biocompatible, and have various times of bioresorption. To this end, the polymers may be further suitable for use in resorbable implantable devices with and without therapeutic agents, device components and/or coatings with and without therapeutic agents for use in other medical systems.

Other resorbable devices that can be advantageously formed from the polymers disclosed herein, and which serve as representative embodiments of useful medical devices, include devices for use in tissue engineering, dental applications, embolotherapy products for the temporary and therapeutic restriction or blocking of blood supply to treat tumors and vascular malformations, and controlled release therapeutic agent delivery devices, as discussed herein. Another embodiment provides a method of treating a body lumen, by deploying within the body lumen a stent according to a medical device embodiment of the present invention.

Unlike 3,5-diodo-4-hydroxyphenylalkanoic acids, conventional methods for creating iodinated diphenolic monomeric species of the present invention through coupling of 3,5-diiodo-4-Hydroxybenzoic Acid to ethylene glycol in refluxing 1,2-dichloroethane with p-toluenesulfonic acid as catalyst are problematic owing to the differing reactivity of the aromatic acid moiety—mostly unreacted starting materials remain. More aggressive reaction conditions to achieve esterification, refluxing in toluene with a sulfuric acid catalyst, did result in more esterification but there was considerable de-iodination of the ring.

Therefore, a method having aspects of the invention include an initial step of preparation of a diphenolic monomeric species in a non-halogenated state, followed by a step including substitution of halogen to create a respective halogenated diphenolic monomeric species, as shown in the examples herein. Advantageously, this approach permits the formation of an iodinated diphenolic structure under reaction conditions that would otherwise either poorly complete the ester linkages, or de-halogenate the aromatic rings.

The non-iodinated diphenolic monomer compound ethane-1,2-diylbis(4-hydroxybenzoate) can be prepared from 4-hydroxybenzoic acid (HBA) by either of two methods, as described below. For convenience, this diphenolic species is abbreviated herein as HBA-EG-HBA.

Aspects of the invention include monomers having the structure of a general formula as follows:

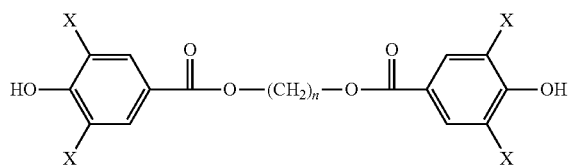

wherein n is an integer from 1 to 18; and wherein each X is independently H or a halogen I or Br, provided that at least one X is iodine. In preferred embodiments, each X is independently H or I, provided that at least one X is iodine. In applications where high radiopacity is valuable or required, each X may be I, so as to give high iodine content.

In one embodiment, a monomer is provided having the structure of Formula Ia:

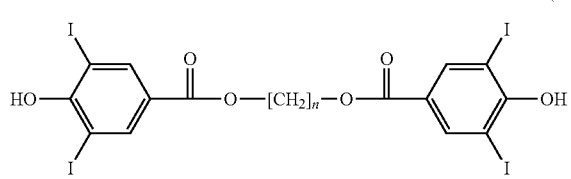

(1a)

wherein n is an integer from 1 to 18.

Aspects of the invention include polymers comprising at least one repeating unit having the structure of a general formula as follows:

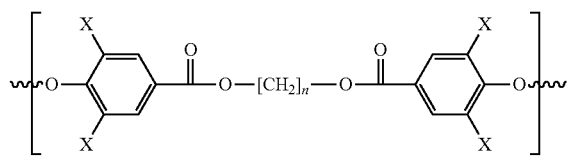

wherein n is an integer from 1 to 18; and wherein each X is independently H or a halogen I or Br, provided that at least one X is iodine. In preferred embodiments, each X is independently H or I, provided that at least one X is iodine. In applications where high radiopacity is valuable or required, each X may be I, so as to give high iodine content.

In another embodiment, a polymer is provided comprising at least one repeating unit having the structure of Formula 1b:

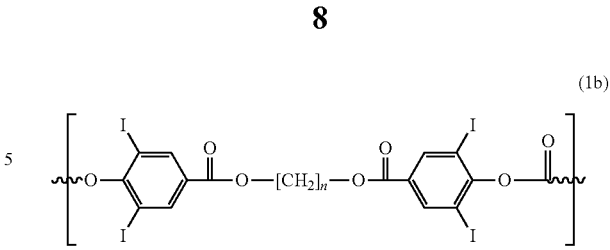

(1b)

wherein n is an integer from 1 to 18.

The presence of the halogen iodine in the monomer and polymer examples above, confer upon these materials the property of radiopacity.

In another embodiment, a polymer is provided comprising at least one repeating unit having the structure of Formula 1b; and further comprising: at least one repeating unit having the structure of either PLLA, PCL, PTMO, PTMC, poly(ethylene glycol), or combinations thereof.

Based on the foregoing, additional embodiments of the compounds, monomers, and polymers of the present invention are discussed herein and will be apparent to one of ordinary skill in the art.

Based on the foregoing, additional embodiments of the compounds, monomers, and polymers of the present invention are discussed herein and will be apparent to one of ordinary skill in the art.

DETAILED DESCRIPTION OF PREFERRED EMBODIMENTS

Novel classes of compounds, monomers, polymers and co-polymers are provided, polymerized from at least one or more repeatable units of an aromatic compound, which include compounds and analogs of compounds that naturally occur in the human body.

Abbreviations and Nomenclature

The following paragraphs provide definitions of various terms used herein.

As used herein, the terms "macromer," "macromeric" and similar terms have the usual meaning known to those skilled in the art and thus may be used to refer to oligomeric and polymeric materials that are functionalized with end groups that are selected so that the macromers can be copolymerized with other monomers. A wide variety of macromers and methods for making them are known to those skilled in the art. Examples of suitable macromers include hydroxy endcapped polylactic acid macromers, hydroxy endcapped polyglycolic acid macromers, hydroxy endcapped poly(lactic acid-co-glycolic acid) macromers, hydroxy endcapped polycaprolactone macromers, poly(alkylene diol) macromers, hydroxy endcapped poly(alkylene oxide) macromers hydroxy endcapped poly(trimethylene carbonate) macromers and hydroxy endcapped polydioxanone macromers.

As used herein, the terms "polymer," "polymeric" and similar terms have the usual meaning known to those skilled in the art and thus may be used to refer to homopolymers, copolymers (e.g., random copolymer, alternating copolymer, block copolymer, graft copolymer) and mixtures thereof.

The term "thermal transition temperature" has the usual meaning known to those skilled in the art and thus may be used to refer to both first order thermal transitions and second order thermal transitions. The first order thermal transition of a polymer or phase thereof may be referred to herein as a "melting point" or Tm", and the second order thermal transition of a polymer or phase thereof may be referred to herein as a "glass transition temperature" or "Tg." Those skilled in the art will appreciate that a polymeric material or phase thereof may have exhibit either or both types of thermal transitions, as well as higher order thermal transitions. Thermal transition temperature may be determined by methods known to those skilled in the art, such as by DSC, DMA, DEA and TMA.

As used herein, the phrase "fracture toughness" means the resistance of a polymer under a static or dynamic load (or strain) to brittle failure from crack propagation within a glassy or semicrystalline phase.

The terms "radiopaque," "radio-opaque," "radiopacity," "radio-opacity," "radiopacifying" and similar terms have the usual meaning known to those skilled in the art and thus may be used to refer to polymer compositions that have been rendered easier to detect using medical imaging techniques (e.g., by X-ray and/or during fluoroscopy) being the incorporation of heavy atoms into the polymer composition. Such incorporation may be by mixing, e.g., by mixing an effective amount of a radiopacifying additive such as barium salt or complex, and/or by attachment of effective amounts of heavy atoms to one or more of the polymers in the polymer composition. For example, attachment of heavy atoms to a polymer in sufficient amounts may advantageously render the polymer easier to detect by various medical imaging techniques. The term "heavy atom" is used herein to refer to atoms having an atomic number of 17 or greater. Preferred heavy atoms have an atomic number of 35 or greater, and include bromine, iodine, bismuth, gold, platinum tantalum, tungsten, and barium. In certain configurations, polymer compositions may be inherently radiopaque. The term "inherently radiopaque" is used herein to refer to a polymer to which a sufficient number of heavy atoms are attached by covalent or ionic bonds to render the polymer radiopaque. This meaning is consistent with the under-standing of those skilled in the art, see, e.g., U.S. Patent Publication No. 2006/0024266, which is hereby incorporated by reference for all purposes, including for the particular purpose of describing radiopaque polymeric materials.

The terms "alkyl", "alkylene" and similar terms have the usual meaning known to those skilled in the art and thus may be used to refer to straight or branched hydro-carbon chain fully saturated (no double or triple bonds) hydrocarbon group. Terminal alkyl groups, e.g., of the general formula —$C_nH_{2n+1}$, may be referred to herein as "alkyl" groups, whereas linking alkyl groups, e.g., of the general formula —$(CH_2)_n$—, may be referred to herein as "alkylene" groups. The alkyl group may have 1 to 50 carbon atoms (whenever it appears herein, a numerical range such as "1 to 50" refers to each integer in the given range; e.g., "1 to 50 carbon atoms" means that the alkyl group may consist of 1 carbon atom, 2 carbon atoms, 3 carbon atoms, etc., up to and including 50 carbon atoms, although the present definition also covers the occurrence of the term "alkyl" where no numerical range is designated). The alkyl group may also be a medium size alkyl having 1 to 30 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl and the like.

The alkyl group may be substituted or unsubstituted. When substituted, the substituent group(s) is(are) one or more group(s) individually and independently selected from lower alkyl, alkenyl, alkynyl, cycloalkyl, cycloalkenyl, cycloalkynyl, aryl, hydroxyaryl, heteroaryl, heteroalicyclyl, aralkyl, heteroaralkyl, (heteroalicyclyl)alkyl, hydroxy, protected hydroxyl, alkoxy, aryloxy, acyl, carboxyl, ester, mercapto, cyano, halogen, carbonyl, thiocarbonyl, O-carbamyl, N-carbamyl, I-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

The terms "alkenyl," "alkenylene" and similar terms have the usual meaning known to those skilled in the art and thus may be used to refer to an alkyl or alkylene group that contains in the straight or branched hydrocarbon chain one or more double bonds. An alkenyl group may be unsubstituted or substituted. When substituted the substituent(s) may be selected from the same groups disclosed above with regard to alkyl group substitution unless otherwise indicated.

The terms "heteroalkyl," "heteroalkylene" and similar terms have the usual meaning known to those skilled in the art and thus may be used to refer to an alkyl group or alkylene group as described herein in which one or more of the carbons atoms in the backbone of alkyl group or alkylene group has been replaced by a heteroatom such as nitrogen, sulfur and/or oxygen. Likewise, the term "heteroalkenylene" may be used to refer to an alkenyl or alkenylene group in which one or more of the carbons atoms in the backbone of alkyl group or alkylene group has been replaced by a heteroatom such as nitrogen, sulfur and/or oxygen.

The term "aryl" has the usual meaning known to those skilled in the art and thus may be used to refer to a carbocyclic (all carbon) monocyclic or multicyclic aromatic ring system that has a fully delocalized pi-electron system. Examples of aryl groups include, but are not limited to, benzene, naphthalene and azulene. The ring of the aryl group may have 5 to 50 carbon atoms. The aryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfon-amido, and amino, including mono- and di-substituted amino groups, and the protected derivatives thereof, unless the substituent groups are otherwise indicated. An aryl group substituted with alkyl may be referred to herein as "alkylaryl."

The term "heteroaryl" has the usual meaning known to those skilled in the art and thus may be used to refer to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The ring of the heteroaryl group may have 5 to 50 atoms. The heteroaryl group may be substituted or unsubstituted. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thia-diazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

The term "crystallizable" has the usual meaning known to those skilled in the art, see U.S. Patent Publication No. 20060024266, which is incorporated herein by reference for all purposes and particularly for the purpose of describing crystallizable groups. Polymers that contain crystallizable groups that are attached to the sides of the polymer, known as side chain crystallizable (SCC) polymers or "comb-like" polymers, are well known, see N. A. Plate and V. P. Shibaev, J. Polymer Sci.: Macromol. Rev. 8:117-253 (1974), the disclosure of which is hereby incorporated by reference. In an embodiment, a polymer as described herein contains crystallizable side groups and thus may be regarded as a SCC polymer. It will be understood that the crystallizable side chains of SCC polymers are preferably selected to crystallize with one another to form crystalline regions and may comprise, for example, —$(CH_2)_x$— and/or —$((CH_2)_b$—O-)y groups. The side chains are preferably linear to facilitate crystallization. For SCC polymers that contain —$(CH_2)_x$— groups in the crystallizable side chain, x is preferably in the range of about 6 to about 30, more preferably in the range of about 20 to about 30. For SCC polymers that contain —$((CH_2)_y$—O—)$_x$— groups in the crystallizable side chain, x is preferably in the range of about 6 to about 30 and y is preferably in the range of about 1 to about 8. More preferably, x and y are selected so that the ($(CH_2)_y$—O—)$_x$ groups contain from about 6 to about 30 carbon atoms, even more preferably from about 20 to about 30 carbon atoms. The spacing between side chains and the length and type of side chain are preferably selected to provide the resulting SCC polymer with a desired melting point. As the spacing between side chains increases, the tendency for the side chains to be crystallizable tends to decrease. Likewise, as the flexibility of the side chains increases the tendency for the side chains to be crystallizable tends to decrease. On the other hand, as the length of the side chains increases, the tendency for the side chains to be crystallizable tends to increase. In many cases, the length of the crystallizable side chain may be in the range of about two times to about ten times the average distance between crystallizable side chains of the SCC polymer.

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents.

Unless otherwise indicated, when a substituent is deemed to be "optionally substituted," or "substituted" it is meant that the substituent is a group that may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Similarly, the term "optionally ring-halogenated" may be used to refer to a group that optionally contains one or more (e.g., one, two, three or four) halogen substituents on the aryl and/or heteroaryl ring. The protecting groups that may form the protective derivatives of the above substituents are known to those of skill in the art and may be found in references such as Greene and Wuts, Protective Groups in Organic Synthesis, 3rd Ed., John Wiley & Sons, New York, N.Y., 1999, which is hereby incorporated by reference in its entirety.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound having one or more double bond(s) generating geometrical isomers that can be defined as E or Z each double bond may independently be E or Z a mixture thereof. Likewise, all tautomeric forms are also intended to be included.

As used herein, the abbreviations for any protective groups, amino acids and other compounds are, unless indicated otherwise, in accord with their common usage, recognized abbreviations, or the IUPAC-IUP Commission on Biochemical Nomenclature (See, Biochem. 11:942-944 (1972)).

Polymer Compositions and Methods

An embodiment is provided in which the "X" groups are selected so that the monomers and polymers are derivatives of hydroxy-arylcarboxylic acids wherein the aryl group is a phenyl, phenoxyphenyl or indole ring. Examples of such acids include 4-4-hydroxybenzoic acid, 5-hydroxy-1H-indol-3-yl-carboxylic acid, and the like. Hydroxy-arylcarboxylic acids from which monomers and polymers may be derived have the structure of Formula Ib, and compounds in which the "X" groups are all oxygens have the structure:

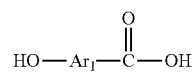

wherein $Ar_1$ and the preferred species thereof, are the same as described above with respect to Formula Ib.

Monomers and polymers derived from 4-hydroxybenzoic acid are preferred, but not necessarily limiting to the present invention. According to an embodiment of the present invention, polyesters are provided, formed by self-condensation of the Formula Ib hydroxy-arylcarboxylic acids and having the structure of Formula IVb:

(IVb)

wherein $Ar_1$ and the preferred species thereof, are the same as described above with respect to Formula Ib, including embodiments wherein $Ar_1$ is a radio opaque phenyl (e.g., iodinated phenyl), phenoxyphenyl or indole ring. Sulfur and amino analogs of the Formula Ib monomers can be used to polymerize sulfur and amine analogs of the Formula IVb polymers.

The monomers of Formula Ib may be polymerized to form the polymers of Formula IVb utilizing any standard esterification reaction known in the art. Polyester block copolymer with any of the other embodiments discussed herein may also be prepared.

The advantageous physical properties of the 4-hydroxybenzoic acid, in no particular order of importance, include the lack of a chiral center, so that, unlike amino acids, it does not give rise to enantiomers when coupled in the foregoing form. Also, because the COOH groups are not on a chiral carbon, there is no racemization during coupling to make the monomer. One embodiment copolymerizes Formula Ia compounds with Formula Ib compounds. When the Formula Ia compound is a hydroxyalkanoic acid such as lactic acid or glycolic acid, and the Formula Ib compound is a hydroxy-arylcarboxylic acid the two compounds are reacted in a polyesterification reaction using carbodiimide coupling agents or thionyl chloride or using acetic anhydride as follows:

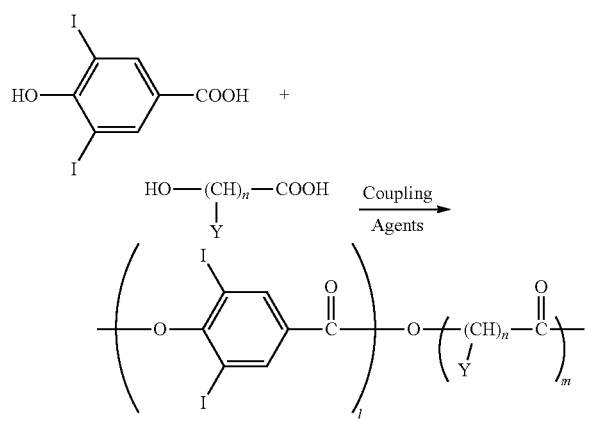

In the depicted embodiment the hydroxy-arylcarboxylic acid is the radio-opaque 3,5-diiodinated 4-hydroxy-benzoic acid, and Y is hydrogen or methyl so the hydroxyalkanoic acid is glycolic acid or lactic acid. When the hydroxyarylcarboxylic acid is radio-opaque, the ratio of m and n is selected to get the desired degree of radio-opacity. In the depicted embodiment, the resulting polymer is a radio-opaque PGA, PLA or PLGA copolymerized with 4-hydroxy-benzoic acid. The molar quantity of m for any iodinated hydroxy-arylcarboxylic acid, or sulfur or amino analog thereof, will range between about 5 and about 95 mol %. Embodiments also include molar quantities of m ranging between about 10 and about 65 mol %, between about 15 and about 60 mol %, between about 20 and about 55 mol %, between about 25 and about 50 mol % and between about 30 and about 45 mol %.

Formula IIa compounds are prepared by reacting either approximately one mole (f=0) or approximately two moles (f=1) of one or more Formula Ib compounds with approximately one mole of a compound having the structure of Formula Ic:

$$HX_3{-}B{-}X_4H \qquad (Ic)$$

to provide a compound having the structure of Formula IIa:

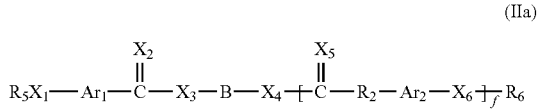
(IIa)

wherein f, $X_1$, $X_2$, $X_3$, $X_4$, $X_5$, $X_6$, $R_2$, $R_3$, $R_5$, $R_6$, $Ar_1$, $Ar_2$, and B, and the preferred species thereof, are the same as previously described.

When the Formula Ib compound is a hydroxy-arylcarboxylic acid, such as 4-hydroxybenzoic acid (HBA), and the Formula Ic compound is a diol, the two compounds are reacted in an acid catalyzed Fischer Esterification reaction as follows:

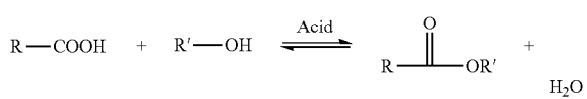

Because this reaction is reversible, removing water from the reaction mixture shifts the equilibrium to the right. Water removal is usually accomplished by way of azeotropic distillation; however other techniques known in the art may be employed as well. In instances where azeotropic distillation is desired, the solvent used for the reaction is carefully chosen so that it forms an azeotropic mixture with water. Generally, solvents such as toluene, heptane, chloroform, tetrachloethylene are preferred.

The main advantage of this reaction is that primary and secondary alcohols form esters with carboxylic acids under acid catalysis, whereas aromatic ring hydroxy groups are non-reactive under these conditions. Thus the carboxylic acid groups of Formula Ib, in the non-iodinated form, can be reacted with primary or secondary alcohols while the phenolic groups remain intact. An example of the foregoing is as follows:

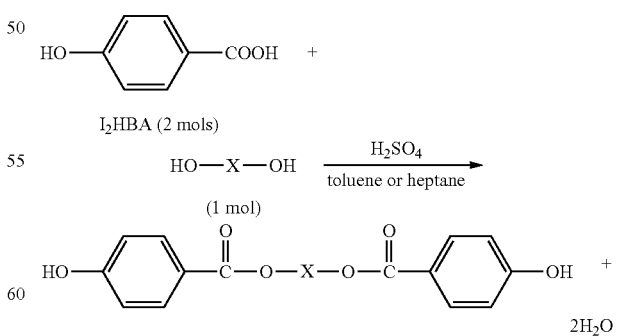

The benzene rings of the resulting diester can be iodinated with $I_2/H_2O_2$ in aqueous ethanol containing sulfuric acid. The X group in the foregoing is equivalent to the B group of Formula IIa, and may be any of the embodiments of B and the preferred species thereof. In the depicted embodiment, HO—X—OH can represent simple alkane diols such as 1,3-propane diol or macromer diols such as poly(ethylene glycol), hydroxy endcapped polycaprolactone-diol, hydroxy endcapped PLA, hydroxy endcapped PGA, hydroxy endcapped PLGA, etc.

When the Formula Ib compound is a hydroxy-arylcarboxylic acid, such as BAT, the Formula IIa compounds contain diphenolic groups that can be polymerized, for example into polycarbonates by reaction with phosgene. When X in the depicted embodiment is PLA, PGA or PLGA, the polymer obtained is a radio-opaque copolymer of PLA, PGA or PLGA.

In certain embodiments, some of the macromer-diols such as hydroxy endcapped polycaprolactone-diol and poly(ethylene glycol) are commercially available. In some cases when such macromer diols as in the case poly(lactic acid)-diol were not available, they were prepared using an alkane diol as the initiator.

In further embodiments, B of Formula IIa is comprised of an macromeric alkyl group of a straight or branched chain alkyl group containing from 1 to 18 carbon atoms. In more specific embodiments, n is 3, 4, 5 or 6.

New Formula IIb polymers may be formed from the Formula IIa monomers of the present invention, in the same fashion as the desaminotyrosyl-tyrosine alkyl ester-derived polymers disclosed before. In one embodiment the Formula IIa diphenol monomers may be polymerized to form a polycarbonate, polyester, poly(phosphazine), poly(phosphoester) or poly(iminocarbonate). This embodiment may be represented by formula IIc:

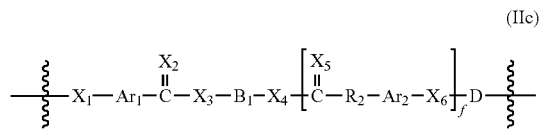

(IIc)

wherein each of $X_1$, $X_2$, $X_3$, $X_4$, $X_5$, $X_6$, $Ar_1$, $Ar_2$, $R_2$ and B, and the embodiments thereof, are the same as described above and D is selected from:

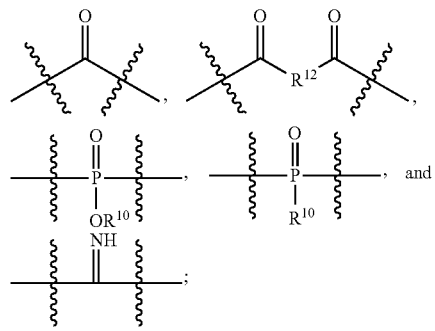

wherein $R_{10}$ is selected from H, an optionally substituted alkyl group, an optionally substituted heteroalkyl group, an optionally substituted alkenyl group and an optionally substituted heteroalkenyl group, each optionally crystallizable and containing from one to 30 carbon atoms, and $R_{12}$ is selected from an optionally substituted alkyl group, an optionally substituted heteroalkyl group, an optionally substituted alkenyl group and an optionally substituted heteroalkenyl group, each containing from one to 18 carbon atoms and an optionally substituted alkylaryl group, an optionally substituted heteroalkylaryl group, an optionally substituted alkenylaryl group and an optionally substituted heteroalkenylary group, each containing up to 12 carbon atoms. One of ordinary skill in the art will understand that the placement of D in a position adjacent to $X_6$ is not limiting to the present invention and that D may also be positioned adjacent to $X_1$ to achieve similar effects, as discussed herein.

Based on the foregoing, in certain embodiments of Formula IIc, D is a carbonyl group having the following structure:

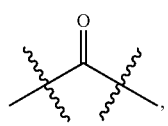 [SMILES: *C(*)=O]

wherein the carbonyl group is derived from a phosgene starting material. This method is essentially the conventional method for polymerizing diols into polycarbonates. Suitable processes, associated catalysts and solvents are known in the art and are taught in Schnell, Chemistry and Physics of Polycarbonates, (Interscience, New York 1964), the teachings of which are incorporated herein by reference. Because X1 and X6 are independently selected from O, S and $NR_3$, the reaction of formula III monomers with phosgene may also produce urethane linkages (—$NR_3$—C(=O)—$NR_3$—), carbonodithioate linkages (—S—(C=O)—S—), carbamate linkages (—O—(C=O)—$NR_3$—), thiocarbonate linkages (—S—(C=O)—O—) and thiocarbamate linkages (—S—(C=O)—$NR_3$—). Other methods adaptable for use to prepare the polycarbonate and other phosgene-derived polymers of the present invention are disclosed in U.S. Pat. Nos. 6,120,491 and 6,475,477 the disclosures of which are incorporated by reference.

In another embodiment, D of Formula IIc is a group having the structure:

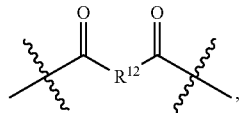

which is derived from a carboxylic acid starting material. When the monomer of Formula IIa is a diphenol, the Formula IIc polymer is formed by reaction of the diphenol with an aliphatic or aromatic dicarboxylic acid in the carbodiimide mediated process disclosed by U.S. Pat. No. 5,216,115 using 4-(dimethylamino) pyridinium-p-toluene sulfonate (DPTS) as a catalyst. The disclosure of U.S. Pat. No. 5,216,115 is incorporated by reference.

The foregoing process forms polymers with —O—C(=O)—$R_{12}$—C(=O)—O— linkages. $R_{12}$ may be selected so the dicarboxylic acids employed as starting materials are either important naturally-occurring metabolites or highly biocompatible compounds. Aliphatic dicarboxylic acid starting materials therefore include the intermediate dicarboxylic acids of the cellular respiration pathway known as the Krebs Cycle. The dicarboxylic acids include alpha-ketoglutaric acid, succinic acid, fumaric acid and oxaloacetic acid ($R_{12}$ may be —$CH_2$—$CH_2$—C(=O)—, —$CH_2$—$CH_2$—, —CH=CH— and —$CH_2$—C(=O)—, respectively).

Yet another naturally occurring aliphatic dicarboxylic acid is adipic acid ($R_{12}$ is (—$CH_2$—)$_4$), found in beet juice. Still another biocompatible aliphatic dicarboxylic acid is sebacic acid ($R_{12}$ is (—$CH_2$—)$_8$), which has been studied extensively and has been found to be nontoxic as part of the clinical evaluation of poly(bis(p-carboxyphenoxy)propane-co-sebacic acid anhydride) by Laurencin et al., J. Biomed. Mater. Res., 24, 1463-81 (1990).

Other biocompatible aliphatic dicarboxylic acids include oxalic acid ($R_{12}$ is a bond), malonic acid ($R_{12}$ is —$CH_2$—), glutaric acid ($R_{12}$ is (—$CH_2$—)$_3$), pimelic acid ($R_{12}$ is (—$CH_2$—)$_5$), suberic acid ($R_{12}$ is (—$CH_2$—)$_6$) and azelaic acid ($R_{12}$ is (—$CH_2$—)$_7$). $R_{12}$ can thus represent (—$CH_2$—)Q, where Q is between 0 and 8, inclusive. Among the suitable aromatic dicarboxylic acids are terephthalic acid, isophthalic acid and bis(p-carboxy-phenoxy) alkanes such as bis(p-carboxy-phenoxy) propane.

$R_{12}$ can also have the structure:

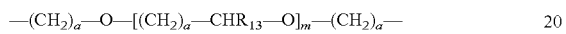

wherein a is 1, 2 or 3, inclusive, m is from 1 to 500,000, inclusive, and $R_{13}$ is hydrogen or a lower alkyl group containing from one to four carbon atoms. $R_{13}$ is preferably hydrogen, a is preferably 1, and m is preferably between about 10 and about 100, and more preferably between about 10 and about 50.

Alternatively, $R_{12}$ can also have the structure:

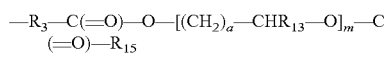

wherein a, m and $R_{13}$ and the preferred species thereof are the same as described above. $R_{15}$ is selected from a bond or straight and branched alkyl and alkylaryl groups containing up to 18 carbon atoms.

The following structure illustrates monomer compounds that are formed when a diacetate of Formula Ib is reacted with phosgene:

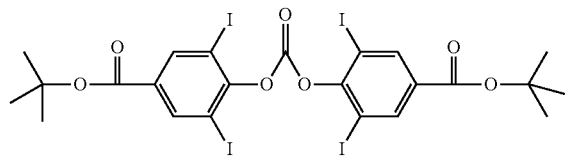 [SMILES: CC(C)(C)OC(=O)c1cc(I)c(OC(=O)Oc2c(I)cc(C(=O)OC(C)(C)C)cc2I)c(I)c1]

di-tert-butyl 4,4'-(carbonylbis(oxy))bis(3,5-diiodo-benzoate)

The other compounds of Formula Ib react similarly. Upon removal of the acetate groups the following dicarboxylic acid is obtained:

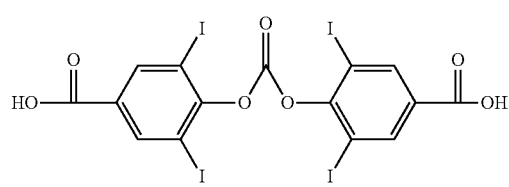

4,4'-(carbonylbis(oxy))bis(3,5-diiodobenzoic acid)

The depicted monomer compounds are dicarboxylates and have a structure depicted by Formula IIIa:

(IIIa)

wherein $X_1$, $X_2$, $X_3$, $X_4$, $X_5$, and $X_6$ are independently selected from the group consisting of O, S and $NR_3$ wherein $R_3$ is selected from the group consisting of hydrogen and alkyl groups containing from one to six carbon atoms;

$Ar_1$ and $Ar_2$ are independently selected from the group consisting of phenylene,

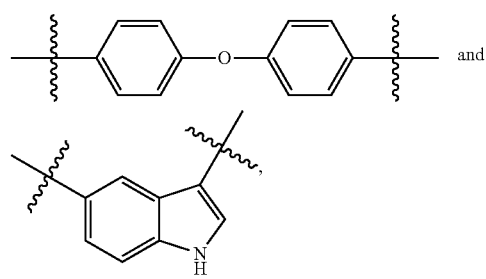

optionally substituted with from one to four substituents independently selected from the group consisting of halogen, halomethyl, halomethoxy, methyl, methoxy, thiomethyl, nitro, sulfoxide, and sulfonyl;

$R_2$ is independently a bond or independently selected from the group consisting of an optionally substituted alkyl, heteroalkyl, alkenyl and heteroalkenyl groups containing from one to ten carbon atoms; $R_5$ and $R_6$ are independently selected from the group consisting of hydrogen and alkyl groups containing from one to six carbon atoms; and B is a carbonyl group.

The Formula IIIa monomers are polymerized according to conventional dicarboxylate polymerization processes to form polyesters, polyamides, and the like, and the sulfur and amino analogs thereof, having the structure of Formula IIIB:

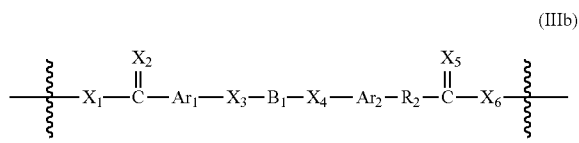

(IIIb)

wherein each of $X_1$, $X_2$, $X_3$, $X_4$, $X_5$, $X_6$, $Ar_1$, $Ar_2$, $R_2$ and B, and the embodiments thereof, are the same as described above for Formula IIIa.

Polymers according to Formula IIb and Formula IIIb include block copolymers with a hydroxy endcapped macromer, a mercapto endcapped macromer or an amino endcapped macromer. Macromer blocks are selected that are also reactive with the co-monomer with which the Formula IIa or Formula Ma monomer is being copolymerized. For example, a hydroxy endcapped macromer can be added to the reaction between a Formula IIa diphenol and phosgene to form a polycarbonate macromer block copolymer, or it can be added to the reaction between a Formula IIa diphenol and a dicarboxylic acid to form a polyarylate macromer block copolymer.

Molar fractions of macromer units range from greater than zero to less than one and are typically greater than zero up to about 0.5. Embodiments include an macromer molar fraction between about 0.10 and about 0.25.

It is difficult to prepare polymers with pendent free carboxylic acid groups by polymerization of corresponding monomers with pendent free carboxylic acid groups without cross-reaction of the free carboxylic acid group with the co-monomer. Accordingly, polymers having pendent free carboxylic acid groups are preferably prepared from the corresponding benzyl and tert-butyl ester polymers (R4 is a benzyl or t-butyl group).

The benzyl ester polymers may be converted to the corresponding free carboxylic acid polymers through the selective removal of the benzyl groups by the palladium catalyzed hydrogenolysis method disclosed in U.S. Pat. No. 6,120,491, the disclosure of which is incorporated herein by reference, and particularly for the purpose of describing such methods. The tert-butyl ester polymers may be converted to the corresponding free carboxylic acid polymers through the selective removal of the tert-butyl groups by the acidolysis method disclosed in U.S. Patent Publication No. 20060034769, also incorporated herein by reference, and particularly for the purpose of describing such methods. The catalytic hydrogenolysis or acidolysis is preferable because the lability of the polymer backbone tends to discourage the employment of harsher hydrolysis techniques.

The molar fraction of free carboxylic acid units in the polymers described herein can be adjusted to modify the degradation of devices made from such polymers. For example, polymers with lower amounts of free carboxylic acid will tend to have longer lifetimes in the body. Further, by otherwise adjusting the amount of free carboxylic acid in the polymers across the range of preferred molar fraction, the resulting polymers can be adapted for use in various applications requiring different device lifetimes. In general, the higher the molar fraction of free carboxylic acid units, the shorter the lifetime of the device in the body and more suitable such devices are for applications wherein shorter lifetimes are desirable or required.

Polymers with a sufficient number of aromatic rings that are sufficiently substituted with bromine or iodine are inherently radiopaque. Various aromatic rings in both the first polymer phase and the second polymer phase can be iodine or bromine substituted. For example, independent of any particular polymer embodiment, the aromatic rings of the recurring units of the formula (I) may be substituted with at least one iodine or bromine atom, on at least one and preferably on both ring positions. In an embodiment, at least 50% of the aromatic rings of recurring units of the formula (I) in a polymer composition are substituted with from two to four iodine or bromine atoms.

The radiopaque monomers may be prepared according to the disclosure of U.S. Pat. No. 6,475,477, or the disclosure of U.S. Patent Publication No. 2006/0034769, the disclosures of both of which are incorporated herein by reference, and particularly for the purpose of describing such monomers and methods of making them. The iodinated and brominated phenolic monomers described herein can also be employed as radiopacifying, biocompatible non-toxic additives for biocompatible polymer compositions, as provided herein. Iodinated and brominated polymers may be polymerized from iodinate and brominated monomers, or the polymers can be iodinated or brominated after polymerization.

In another radiopaque polymer embodiment, methylene hydrogens are replaced with bromine or iodine to increase polymer radio-opacity. Such substitution may be concurrent with or in place of halogen substituted phenyl groups, as discussed above. Accordingly, radio-opaque polylactic acids, polyglycolic acids and polylactic-co-glycolic acids are provided by replacing a sufficient number of methylene hydrogens with bromine, iodine or both. A preferred radio-opaque polylactic acid contains lactic acid units with pendant triiodomethyl groups.

After polymerization of any of the foregoing compounds or monomers, appropriate work up of the polymers in accordance with preferred embodiments of the present invention may be achieved by any of a variety of known methods commonly employed in the field of synthetic polymers to produce a variety of useful articles with valuable physical and chemical properties.

Medical Uses

Various embodiments of the polymer compositions described herein, preferably derived from tissue compatible monomers, may be used to produce a variety of useful articles with valuable physical and chemical properties. The useful articles can be shaped by conventional polymer thermo-forming techniques such as extrusion and injection molding when the degradation temperature of the polymer is above the glass transition or crystalline melt temperature(s), or conventional non-thermal techniques can be used, such as compression molding, injection molding, solvent casting, spin casting, wet spinning. Combinations of two or more methods can be used. Shaped articles prepared from the polymers are useful, inter alia, as biocompatible, biodegradable and/or bioresorbable biomaterials for medical implant applications.

In one embodiment, the medical device is a stent. It is contemplated that a stent may comprise many different types of forms. For instance, the stent may be an expandable stent. In another embodiment, the stent may be configured to have the form of a sheet stent, a braided stent, a self-expanding stem, a woven stent, a deformable stent, or a slide-and-lock stent. Stent fabrication processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms.

In certain other embodiments, the polymers are formed into coatings on the surface of an implantable device, particularly a stent, made either of a polymer of the present invention or another material, such as metal. Such coatings may be formed on stents via techniques such as dipping, spray coating, combinations thereof, and the like. Further, stents may be comprised of at least one fiber material, curable material, laminated material, and/or woven material. The medical device may also be a stent graft or a device used in embolotherapy.

Details of stent products and fabrication in which the polymers disclosed herein may be employed are disclosed in US Pat. Publication No. 2006/0034769, the disclosure of which is incorporated by reference. Stents are preferably fabricated from the radiopaque polymers of the present invention, to permit fluoroscopic positioning of the device.

The highly beneficial combination of properties associated with the polymers disclosed herein means these polymers are well-suited for use in producing a variety of resorbable medical devices besides stents, especially implantable medical devices that are preferably radiopaque, biocompatible, and have various times of bioresorption. For example the polymers are suitable for use in resorbable implantable devices with and without therapeutic agents, device components and/or coatings with and without therapeutic agents for use in other medical systems, for instance, the musculoskeletal or orthopedic system (e.g., tendons, ligaments, bone, cartilage skeletal, smooth muscles); the nervous system (e.g., spinal cord, brain, eyes, inner ear); the respiratory system (e.g., nasal cavity and sinuses, trachea, larynx, lungs); the reproductive system (e.g., male or female reproductive); the urinary system (e.g., kidneys, bladder, urethra, ureter); the digestive system (e.g., oral cavity, teeth, salivary glands, pharynx, esophagus, stomach, small intestine, colon), exocrine functions (biliary tract, gall bladder, liver, appendix, recto-anal canal); the endocrine system (e.g., pancreas/islets, pituitary, parathyroid, thyroid, adrenal and pineal body), the hematopoietic system (e.g., blood and bone marrow, lymph nodes, spleen, thymus, lymphatic vessels); and, the integumentary system (e.g., skin, hair, nails, sweat glands, sebaceous glands).

The polymers described herein can thus be used to fabricate wound closure devices, hernia repair meshes, gastric lap bands, drug delivery implants, envelopes for the implantation of cardiac devices, devices for other cardiovascular applications, non-cardiovascular stents such as biliary stents, esophageal stents, vaginal stents, lung-trachea/bronchus stents, and the like.

In addition, the resorbable polymers are suitable for use in producing implantable, radiopaque discs, plugs, and other devices used to track regions of tissue removal, for example, in the removal of cancerous tissue and organ removal, as well as, staples and clips suitable for use in wound closure, attaching tissue to bone and/or cartilage, stopping bleeding (homeostasis), tubal ligation, surgical adhesion prevention, and the like. Applicants have also recognized that the resorbable polymers disclosed herein are well-suited for use in producing a variety of coatings for medical devices, especially implantable medical devices.

In some embodiments, the disclosed polymers may be advantageously used in making various resorbable orthopedic devices including, for example, radiopaque biodegradable screws (interference screws), radiopaque biodegradable suture anchors, and the like for use in applications including the correction, prevention, reconstruction, and repair of the anterior cruciate ligament (ACL), the rotator cuff/rotator cup, and other skeletal deformities.

Other devices that can be advantageously formed from preferred embodiments of the polymers described herein include devices for use in tissue engineering. Examples of suitable resorbable devices include tissue engineering scaffolds and grafts (such as vascular grafts, grafts or implants used in nerve regeneration). The present resorbable polymers may also be used to form a variety of devices effective for use in closing internal wounds. For example biodegradable resorbable sutures, clips, staples, barbed or mesh sutures, implantable organ supports, and the like, for use in various surgery, cosmetic applications, and cardiac wound closures can be formed.

Various devices useful in dental applications may advantageously be formed from disclosed polymer embodiments. For example, devices for guided tissue regeneration, alveolar ridge replacement for denture wearers, and devices for the regeneration of maxilla-facial bones may benefit from being radiopaque so that the surgeon or dentist can ascertain the placement and continuous function of such implants by simple X-ray imaging.

Preferred embodiments of the polymers described herein are also useful in the production of bioresorbable, inherently radiopaque polymeric embolotherapy products for the temporary and therapeutic restriction or blocking of blood supply to treat tumors and vascular malformations, e.g., uterine fibroids, tumors (i.e., chemoembolization), hemorrhage (e.g., during trauma with bleeding) and arteriovenous malformations, fistulas and aneurysms delivered by means of catheter or syringe. Details of embolotherapy products and methods of fabrication in which polymer embodiments described herein may be employed are disclosed in U.S. Patent Publication No. 2005/0106119, the dis-closure of which is incorporated by reference. Embolotherapy treatment methods are by their very nature local rather than systemic and the products are preferably fabricated from radiopaque polymers, such as the radiopaque polymers disclosed herein, to permit fluoroscopic monitoring of delivery and treatment.

The polymers described herein are further useful in the production of a wide variety of therapeutic agent delivery devices. Such devices may be adapted for use with a variety of therapeutics including, for example, pharmaceuticals (i.e., drugs) and/or biological agents as previously defined and including biomolecules, genetic material, and processed biologic materials, and the like. Any number of transport systems capable of delivering therapeutics to the body can be made, including devices for therapeutics delivery in the treatment of cancer, intravascular problems, dental problems, obesity, infection, and the like.

A medical device that comprises a polymeric material may include one or more additional components, e.g., a plasticizer, a filler, a crystallization nucleating agent, a preservative, a stabilizer, a photoactivation agent, etc., depending on the intended application. For example, in an embodiment, a medical device comprises an effective amount of at least one therapeutic agent and/or a magnetic resonance enhancing agent. Non-limiting examples of preferred therapeutic agents include a chemotherapeutic agent, a non-steroidal anti-inflammatory, a steroidal anti-inflammatory, and a wound healing agent. Therapeutic agents may be co-administered with the polymeric material. In a preferred embodiment, at least a portion of the therapeutic agent is contained within the polymeric material. In another embodiment, at least a portion of the therapeutic agent is contained within a coating on the surface of the medical device.

Non-limiting examples of preferred chemotherapeutic agents include taxanes, taxinines, taxols, paclitaxel, dioxorubicin, cis-platin, adriamycin, and bleomycin. Non-limiting examples of preferred non-steroidal anti-inflammatory compounds include aspirin, dexamethasone, ibuprofen, naproxen, and Cox-2 inhibitors (e.g., Rofexcoxib, Celecoxib and Valdecoxib). Non-limiting examples of preferred steroidal anti-inflammatory compounds include dexamethasone, beclomethasone, hydrocortisone, and prednisone. Mixtures comprising one or more therapeutic agents may be used. Non-limiting examples of preferred magnetic resonance enhancing agents include gadolinium salts such as gadolinium carbonate, gadolinium oxide, gadolinium chloride, and mixtures thereof.

The amounts of additional components present in the medical device are preferably selected to be effective for the intended application. For example, a therapeutic agent is preferably present in the medical device in an amount that is effective to achieve the desired therapeutic effect in the patient to whom the medical device is administered or implanted. Such amounts may be determined by routine experimentation. In certain embodiments, the desired therapeutic effect is a biological response. In an embodiment, the therapeutic agent in the medical device is selected to promote at least one biological response, preferably a biological response selected from the group consisting of thrombosis, cell attachment, cell proliferation, attraction of inflammatory cells, deposition of matrix proteins, inhibition of thrombosis, inhibition of cell attachment, inhibition of cell proliferation, inhibition of inflammatory cells, and inhibition of deposition of matrix proteins. The amount of magnetic resonance enhancing agent in a medical devices is preferably an amount that is effective to facilitate radiologic imaging, and may be determined by routine experimentation.

The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" may include 1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent may also include vitamin or mineral substances or other natural elements.

For devices placed in the vascular system, e.g., a stent, the amount of the therapeutic agent is preferably sufficient to inhibit restenosis or thrombosis or to affect some other state of the stented tissue, for instance, heal a vulnerable plaque, and/or prevent rupture or stimulate endothelialization. The agent(s) may be selected from the group consisting of antiproliferative agents, anti-inflammatory, anti-matrix metallo-proteinase, and lipid lowering, cholesterol modifying, anti-thrombotic and antiplatelet agents, in accordance with preferred embodiments of the present invention. In some preferred embodiments of the stent, the therapeutic agent is contained within the stent as the agent is blended with the polymer or admixed by other means known to those skilled in the art. In other preferred embodiments of the stent, the therapeutic agent is delivered from a polymer coating on the stent surface. In another preferred variation the therapeutic agent is delivered by means of no polymer coating. In other preferred embodiments of the stent, the therapeutic agent is delivered from at least one region or one surface of the stent. The therapeutic may be chemically bonded to the polymer or carrier used for delivery of the therapeutic of at least one portion of the stent and/or the therapeutic may be chemically bonded to the polymer that comprises at least one portion of the stent body. In one preferred embodiment, more than one therapeutic agent may be delivered.

In certain embodiments, any of the aforementioned devices described herein can be adapted for use as a therapeutic delivery device (in addition to any other functionality thereof). Controlled therapeutic delivery systems may be prepared, in which a therapeutic agent, such as a biologically or pharmaceutically active and/or passive agent, is physically embedded or dispersed within a polymeric matrix or physically admixed with a polymer described herein. Controlled therapeutic agent delivery systems may also be prepared by direct application of the therapeutic agent to the surface of an implantable medical device such as a bioresorbable stent device (comprised of at least one of the polymers described herein) without the use of these polymers as a coating, or by use of other polymers or substances for the coating.

In certain embodiments, any of the aforementioned devices described herein can be adapted for use as a therapeutic delivery device (in addition to any other functionality thereof). Controlled therapeutic delivery systems may be prepared, in which a therapeutic agent, such as a biologically or pharmaceutically active and/or passive agent, is physically embedded or dispersed within a polymeric matrix or physically admixed with a polymer embodiment. Controlled therapeutic agent delivery systems may also be prepared by direct application of the therapeutic agent to the surface of an implantable medical device such as a bioresorbable stent device (comprised of at least one of the present polymers) without the use of these polymers as a coating, or by use of other polymers or substances for the coating.

The therapeutic agent may first be covalently attached to a monomer, which is then polymerized, or the polymerization may be performed first, followed by covalent attachment of the therapeutic agent. Hydrolytically stable conjugates are utilized when the therapeutic agent is active in conjugated form. Hydrolyzable conjugates are utilized when the therapeutic agent is inactive in conjugated form.

Therapeutic agent delivery compounds may also be formed by physically blending the therapeutic agent to be delivered with the polymer embodiments using conventional techniques well-known to those of ordinary skill in the art. For this therapeutic agent delivery embodiment, it is not essential that the polymer have pendent groups for covalent attachment of the therapeutic agent.

The polymer compositions described herein containing therapeutic agents, regardless of whether they are in the form of polymer conjugates or physical admixtures of polymer and therapeutic agent, are suitable for applications where localized delivery is desired, as well as in situations where a systemic delivery is desired. The polymer conjugates and physical admixtures may be implanted in the body of a patient in need thereof, by procedures that are essentially conventional and well-known to those of ordinary skill in the art.

Implantable medical devices may thus be fabricated that also serve to deliver a therapeutic agent to the site of implantation by being fabricated from or coated with the therapeutic agent delivery system embodiment described herein in which a disclosed polymer embodiment has a therapeutic agent physically admixed therein or covalently bonded thereto, such as a drug-eluting stent. Covalent attachment requires a polymer to have a reactive pendent group. Embolotherapeutic particles may also be fabricated for delivery of a therapeutic agent.

Examples of biologically or pharmaceutically active therapeutic agents that may be physically admixed with or covalently attached to polymer embodiments disclosed herein include acyclovir, cephradine, malphalen, procaine, ephedrine, adriamycin, daunomycin, plumbagin, atropine, quinine, digoxin, quinidine, biologically active peptides, chlorin e6, cephradine, cephalothin, proline and proline analogs such as cis-hydroxy-L-proline, malphalen, penicillin V and other antibiotics, aspirin and other non-steroidal anti-inflammatory compounds, nicotinic acid, chemodeoxycholic acid, chlorambucil, anti-tumor and anti-proliferative agents, including anti-proliferative agents that prevent restenosis, hormones such as estrogen, and the like. Biologically active compounds, for purposes of the present invention, are additionally defined as including cell attachment mediators, biologically active ligands, and the like.

The invention described herein also includes various pharmaceutical dosage forms containing the polymer-therapeutic agent combinations described herein. The combination may be a bulk matrix for implantation or fine particles for administration by traditional means, in which case the dosage forms include those recognized conventionally, e.g. tablets, capsules, oral liquids and solutions, drops, parenteral solutions and suspensions, emulsions, oral powders, inhalable solutions or powders, aerosols, topical solutions, suspensions, emulsions, creams, lotions, ointments, transdermal liquids and the like.

The dosage forms may include one or more pharmaceutically acceptable carriers. Such materials are non-toxic to recipients at the dosages and concentrations employed, and include diluents, solubilizers, lubricants, suspending agents, encapsulating materials, penetration enhancers, solvents, emollients, thickeners, dispersants, buffers such as phosphate, citrate, acetate and other organic acid salts, antioxidants such as ascorbic acid, preservatives, low molecular weight (less than about 10 residues) peptides such as polyarginine, proteins such as serum albumin, gelatin, or immunoglobulins, other hydrophilic polymers such as poly(vinylpyrrolidinone), amino acids such as glycine, glutamic acid, aspartic acid, or arginine, monosaccharides, disaccharides, and other carbohydrates, including cellulose or its derivatives, glucose, mannose, or dextrines, chelating agents such as EDTA, sugar alcohols such as mannitol or sorbitol, counter-ions such as sodium and/or nonionic surfactants such as tween, pluronics or PEG.

Therapeutic agents to be incorporated in the polymer conjugates and physical admixture embodiments disclosed herein may be provided in a physiologically acceptable carrier, excipient stabilizer, etc., and may be provided in sustained release or timed release formulations supplemental to the polymeric formulation prepared in this invention. Liquid carriers and diluents for aqueous dispersions are also suitable for use with the polymer conjugates and physical admixtures.

Subjects in need of treatment, typically mammalian, using the disclosed polymer-therapeutic agent combinations, can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize. The polymer-therapeutic agent combinations may be prepared for storage under conditions suitable for the preservation of therapeutic agent activity as well as maintaining the integrity of the polymers, and are typically suitable for storage at ambient or refrigerated temperatures.

Depending upon the particular compound selected transdermal delivery may be an option, providing a relatively steady delivery of the drug, which is preferred in some circumstances. Transdermal delivery typically involves the use of a compound in solution with an alcoholic vehicle, optionally a penetration enhancer, such as a surfactant, and other optional ingredients. Matrix and reservoir type transdermal delivery systems are examples of suitable transdermal systems. Transdermal delivery differs from conventional topical treatment in that the dosage form delivers a systemic dose of the therapeutic agent to the patient.

The polymer-drug formulation described herein may also be administered in the form of liposome delivery systems, such as small unilamellar vesicles, large unilamellar vesicles and multilamellar vesicles. Liposomes may be used in any of the appropriate routes of administration described herein. For example, liposomes may be formulated that can be administered orally, parenterally, transdermally or via inhalation. Therapeutic agent toxicity could thus be reduced by selective delivery to the affected site. For example if the therapeutic agent is liposome encapsulated, and is injected intravenously, the liposomes used are taken up by vascular cells and locally high concentrations of the therapeutic agent could be released over time within the blood vessel wall, resulting in improved action of the therapeutic agent. The liposome encapsulated therapeutic agents are preferably administered parenterally, and particularly, by intravenous injection.

Liposomes may be targeted to a particular site for release of the therapeutic agent. This would obviate excessive dosages that are often necessary to provide a therapeutically useful dosage of a therapeutic agent at the site of activity, and consequently, the toxicity and side effects associated with higher dosages.

Therapeutic agents incorporated into the polymers of described herein may desirably further incorporate agents to facilitate their delivery systemically to the desired target, as long as the delivery agent meets the same eligibility criteria as the therapeutic agents described above. The active therapeutic agents to be delivered may in this fashion be incorporated with antibodies, antibody fragments, growth factors, hormones, or other targeting moieties, to which the therapeutic agent molecules are coupled.

The polymer-therapeutic agent combinations described herein may also be formed into shaped articles, such as valves, stents, tubing, prostheses, and the like. Cardiovascular stents may be combined with therapeutic agents that prevent restenosis. Implantable medical devices may be combined with therapeutic agents that prevent infection.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rates from the formulations of this invention are also varied within the routine skill in the art to determine an advantageous profile, depending on the therapeutic conditions to be treated.

A typical dosage might range from about 0.001 mg/k/g to about 1,000 mg/k/g, preferably from about 0.01 mg/k/g to about 100 mg/k/g, and more preferably from about 0.10 mg/k/g to about 20 mg/k/g. Advantageously, the compounds of this invention may be administered several times daily, and other dosage regimens may also be useful.

In practicing the methods described herein, the polymer-therapeutic agent combinations may be used alone or in combination with other therapeutic or diagnostic agents. The compounds of this invention can be utilized in vivo, ordinarily in mammals such as primates such as humans, sheep, horses, cattle, pigs, dogs, cats, rats and mice, or in vitro.

An advantage of using the radiopaque, bioresorbable polymers described herein in therapeutic agent delivery applications is the ease of monitoring release of a therapeutic agent and the presence of the implantable therapeutic delivery system. Because the radiopacity of the polymeric matrix is due to covalently attached halogen substituents, the level of radiopacity is directly related to the residual amount of the degrading therapeutic agent delivery matrix still present at the implant site at any given time after implantation. In preferred embodiments the rate of therapeutic release from the degrading therapeutic delivery system will be correlated with the rate of polymer resorption. In such preferred embodiments, the straight-forward, quantitative measurement of the residual degree of radio-opacity will provide the attending physician with a way to monitor the level of therapeutic release from the implanted therapeutic delivery system.

The following non-limiting examples set forth herein below illustrate certain aspects of the invention. All parts and percentages are by mole percent unless otherwise noted and all temperatures are in degrees Celsius unless otherwise indicated. All solvents were HPLC grade and all other reagents were of analytical grade and were used as received, unless otherwise indicated.

EXAMPLES

A method having aspects of the invention includes an initial step of preparation of a diphenolic monomeric species in a non-halogenated state, followed by a step including substitution of halogen to create a respective halogenated diphenolic monomeric species. For example, the diphenolic monomer compound ethane-1, 2-diyl bis(4-hydroxybenzoate) can be prepared from 4-hydroxybenzoic acid (HBA) by either of two methods, as described below. For convenience, this diphenolic species is abbreviated herein as HBA-EG-HBA.

Example 1. Preparation of Ethane-1,2-diyl bis(4-hydroxybenzoate) Using $Sb_2O_3$ as a Catalyst In this method, 4-hydroxybenzoic acid (HBA) is heated with excess ethylene glycol (EG) under reflux using $Sb_2O_3$ as the catalyst. The reaction is continued until close to theoretical amount of water distils off.

Preparation of Ethane-1,2-diyl bis(4-hydroxybenzoate) Using $Sb_2O_3$ as a Catalyst

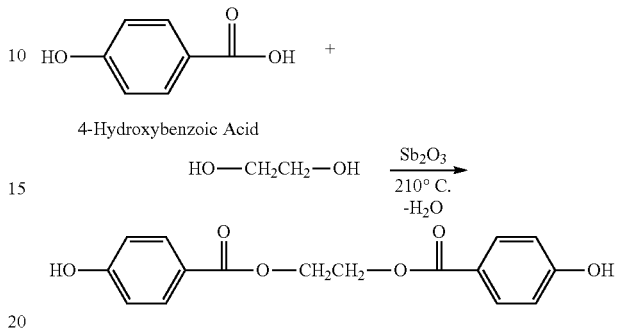

In a 1 L flask 500 g (1.81 mol) of HBA, 250 g (4.02 mol) of ethylene glycol and 0.25 g of $Sb_2O_3$ were heated at 130° C. for 30 min. The temperature was increased to 210° C. and the water liberated was collected by distillation.

After about 32 mL of water had collected, the reaction was stopped and after cooling to room temperature, cold water was added to precipitate the product. The product was isolated by filtration and washed with water. It was purified by recrystallization from acetone and characterized by $^1H$ NMR, HPLC, and elemental analysis.

Example 2. Preparation of Ethane-1,2-diyl bis(4-hydroxybenzoate) by Fisher Synthesis This diphenol can also be prepared by Fisher synthesis by heating mixture of HBA, EG, and catalytic amount of sulfuric acid with toluene under reflux. The water liberated is removed by azeotropic distillation using a Dean-Stark trap. This method is carried at a lower temperature and the product has fewer impurities and is the preferred method.

Preparation of Ethane-1,2-diylbis(4-hydroxybenzoate) by Fisher Synthesis (HBA-EG-HBA)

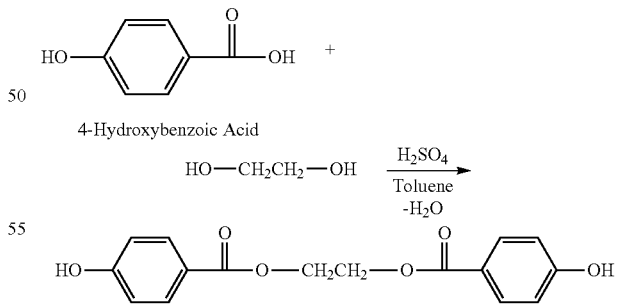

A mixture 4-Hydroxybenzoic acid (140.9 g, 1.02 mol) and ethylene glycol (31.03 g, 0.5 mol) was stirred in a 500 mL flask under nitrogen and to the stirred mixture was added 5.5 mL of sulfuric acid followed by the addition of 250 mL of toluene. The flask was heated to reflux in an oil bath with Dean-stark trap to separate the water liberated. The two-phase system was vigorously stirred to ensure completion of reaction.

When about 18 mL water had collected, the reaction mixture was allowed to cool and the product was isolated by filtration and dried in vacuum oven 40° C. overnight.

To remove sulfuric acid and un-reacted HBA the product was stirred with 5% aqueous sodium bicarbonate, followed by stirring with water. It was isolated by filtration, washed with water, and dried in vacuum oven at 40° C. for 24 h. The product was characterized $^1$H NMR, HPLC, and elemental analysis.

Both of the above methods can be used to synthesize HBA diesters of any alkylene diols, generally of the form HO—$(CH_2)_n$—OH). For example, the methods described above for preparation of ethane-1,2-diyl bis(4-hydroxybenzoate) from ethylene glycol (where n=2), may also be used for the preparation of hexane-1,6-diyl bis(4-hydroxybenzoate from 1,6-hexanediol (where n=6).

Example 3. Iodination of HBA-EG-HBA to Obtain $I_2$HBA-EG-$I_2$HBA

Iodination of the constituent rings of the above diphenol is carried out in ethanol using iodine in the presence of sulfuric acid. 30% aqueous $H_2O_2$ or potassium iodate is used as the oxidizing agent.

The method using $H_2O_2$ is carried out at 60° C., whereas the method using $KIO_3$ typically requires higher temperature (refluxing in aqueous ethanol) which may result in hydrolysis and alcoholysis of the HBA-EG-HBA. Therefore the $H_2O_2$ method is the preferred method.

Tetraiodination of HBA-EG-HBA to Obtain $I_2$HBA-EG-$I_2$HBA

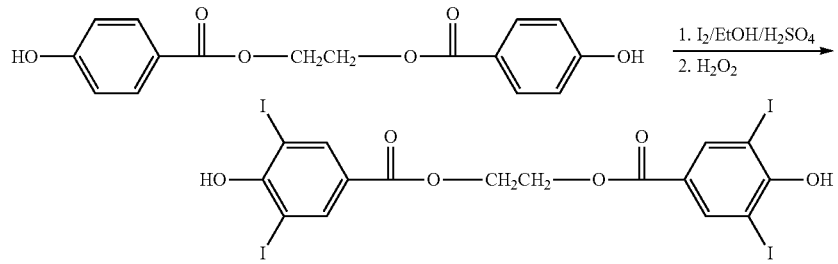

Ethane-1,2-diyl bis(4-hydroxybenzoate) (75.6 g, 0.25 mol) was heated with 250 mL of 95% ethanol to reflux in 1 L round bottomed flask with an overhead stirrer under a $N_2$ atmosphere. The solid partially dissolved and to the suspension was added 139.7 g (0.55 mol) of iodine. Through an addition funnel 39 g (0.07 mol) of potassium iodate dissolved in 440 mL of deionized water was added to the reaction mixture over 15 min. The reaction mixture was heated to reflux for 2 h while stirring vigorously. The reaction mixture was then cooled to room temperature. The pink colored precipitate was isolated by filtration and washed with a 10% $Na_2S_2O_3$ solution followed by washing with water. The product was dried in a vacuum oven at 40° C. The product was purified by recrystallization. Product was characterized by $^1$H NMR, HPLC, and elemental analysis.

The method described above for preparation of $I_2$HBA-EG-$I_2$HBA from HBA-EG-HBA, can also be used for the iodination of the HBA diesters of any alkelene diols of the form HBA-$(CH_2)_n$-HBA. In a specific example, hexane-1,6-diyl bis(4-hydroxybenzoate), abbreviated for convenience here as HBA-HxD-HBA, may be diiodinated to form $I_2$HBA-HxD-$I_2$HBA by this method.

As described above, the process can be employed to provide for diiodination of each phenyl ring of the constituent HBA groups of the HBA-EG-HBA. To maximize the iodine content, the reaction is described below as it is allowed to proceed to completion, so as to produce fully iodinated monomer $I_2$HBA-EG-$I_2$HBA. Alternatively, the reaction may be controlled to produce partially iodinated monomer, whereby generally the diphenolic monomer moiety contains less than four iodine atoms.

Polymerization of the tetraiodinated diester(ethane-1,2-diylbis(4-hydroxy-3,5-diiodobenzoate)) of 4-hydroxybenzoic acid by phosgenation was performed. This monomer was not soluble in chlorinated hydrocarbons such as dichloromethane and chloroform, and 1,2-dichloroethane. The monomer was soluble in tetrahydrofuran (THF) and hence polymerization was carried out in THF.

Example 4. Polymerization of ethane-1,2-diylbis(4-hydroxy-3,5-diiodobenzoate)

Ethane-1,2-diyl bis(4-hydroxy-3,5-diiodobenzoate) (10 g, 12.4 mmol); THF (55 mL) and pyridine (5.6 mL, 71.1 mmol) were stirred in a 250 mL 3-necked round bottomed flask and stirred with an overhead stirrer to get a clear solution. To this solution was added using syringe pump 1.84 g of triphosgene dissolved in 9 mL of Chloroform over 3 h. After the addition was complete the stirring was continued for 30 m and then 100 mL of deionized water was added and stirred for 10 min. Allowed stand for 10 min and the top layer was siphoned out. The reaction mixture was washed as above with another 100 mL portion of deionized water.

The polymer was then precipitated by adding 50 ml of 2-propanol while stirring. The supernatant was siphoned out and to the stirred precipitate 50 mL of IPA was added. The polymer was isolated by filtration as an off-white powder. It was dried in vacuum oven at 55° C. for 24 h. The DSC of the powder gave a Tg of 169.7° C. (2 nd heat, broad transition).

Example 5. Co-Polymerization of ethane-1,2-diylbis(4-hydroxy-3,5-diiodobenzoate) with poly(trimethylene carbonate)

Ethane-1,2-diylbis(4-hydroxy-3,5-diiodobenzoate) (15 g, 18.6 mmol) and poly(trimethylene carbonate) (10 g, 1.0 mmol, Mn=10000); and THF (135 mL) were stirred in a 500 mL, 3-necked round-bottomed flask. To the stirred solution was added using syringe pump 2.52 g (8.50 mmol) of triphosgene dissolved in 12 mL of chloroform over 3 h. After the addition was complete the stirring was continued for 30 m and then 200 mL of deionized water was added and stirred for 10 min. Allowed stand for 10 min and the top layer was siphoned out. The reaction mixture was washed as above with another 200 mL portion of deionized water.

The polymer was then precipitated by adding 100 ml of 2-propanol while stirring. The supernatant was siphoned out and to the stirred precipitate 100 mL of IPA was added. The polymer was isolated by filtration as stringy off-white particles. It was dried in vacuum oven at 55° C. for 3 days. The DSC of the powder showed two distinct Tgs, one at 111° C. and the second at 167.6° C. ($1^{st}$ heat, broad transition).

Example 6. Iodination of HBA-EG-HBA Using $H_2O_2$

In a 500 mL flask a mixture of 20 g of HBA-EG-HBA, 34 g of iodine, 100 mL of 95% ethanol, and 9 mL of sulfuric acid was stirred with a magnetic stirrer and heated to 60° C. using a water bath. To this was then added 21 mL of 30% aqueous $H_2O_2$ using an addition funnel over 30 min.

After stirring for 30 min, the mixture was cooled and added to 400 mL of water with stirring. The precipitate was isolated by filtration and washed with 2 100 mL portions of acetic acid and then with 2 100 mL portions of acetone. The product was dried in a vacuum oven at 40° C. It was characterized by $^1$H NMR, HPLC, and elemental analysis. Polymers of Recurring Units of $I_2HBA-(CH_2)_n-I_2HBA$.

Polycarbonate polymers and copolymers having recurring units of $I_2HBA-(CH_2)_n-I_2HBA$ as described in the above example may be made by the methods described in U.S. Pat. No. 8,252,887, among other ways. Repeat unit of $I_2HBA-(CH_2)n-I_2HBA$ in a polycarbonate:

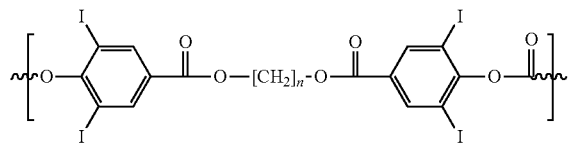

The examples below demonstrate a substantial range of chemically-similar moieties for $(CH_2)_n$ in FIG. 4, and in particular ethane-1,2-diylbis(4-hydroxybenzoate) where n=2, and hexane-1,6-diylbis(4-hydroxybenzoate) where n=6.

Example 7. Polymerization of ethane-1,2-diyl bis(4-hydroxybenzoate) (HBA-EG-HBA Into a 500 mL, 3-necked round bottomed flask were added 25 g (0.083 mol) of ethane-1,2-diyl bis(4-hydroxybenzoate), 135 mL of chloroform, and 27 g (0.34 mol) of pyridine and stirred under positive nitrogen pressure. To the flask was then added a solution of 9 g (0.030 mol) of triphosgene in 24 mL of chloroform over 3 h using a syringe pump. Initially the monomer did not completely dissolve. When about ⅓ of the triphosgene solution had been added the reaction mixture became clear. Again when about ⅔ of the addition was complete solids began to precipitate and the polymer precipitated completely at the end of the addition. To the flask was added a mixture of 24 mL of THF and 1 mL of water to quench the reaction. This was followed by the addition of 250 mL of 2-propanol (IPA). The precipitate was collected by filtration. To further purify the polymer 150 mL of dichloromethane (DCM) was added to it and stirred for 30 min. 250 mL IPA was added to the swollen gel and the precipitate was further stirred with 250 mL acetone and then collected by filtration. The product was dried in vacuum oven at 45° C. for 24 h and 55° C. for 2 days. The molecular weight of the polymer was low. The compression molded films prepared at 240° C. were brittle. Higher molecular weight polymers can be made by routine optimization of reaction conditions.

DSC of the dried sample showed a Tm of 214.5° C. with a ΔH of 49.6 J/g (1st) heat and Tg of 92.1° C. (2nd heat).

Example 8. Polymerization of hexane-1,6-diyl bis(4-hydroxybenzoate)

Into a 500 mL, 3-necked round bottomed flask were added 25 g (0.083 mol) of hexane-1,6-diyl bis(4-hydroxybenzoate), 135 mL of chloroform, and 23 g (0.29 mol) of pyridine and stirred under positive nitrogen pressure. A clear solution resulted. To the flask was then added a solution of 7.6 g (0.026 mol) of triphosgene in 21 mL of chloroform over 3 h using a syringe pump. To the flask was added a mixture of 24 mL of THF and 1 mL of water to quench the reaction. This was followed by the addition of 250 mL of 2-propanol (IPA) when the product precipitated as gel. The gel was ground with 750 mL of IPA in a blender. The precipitated solid was isolated by filtration and re-dissolved in 150 mL of DCM. The resulting solution was first precipitated with 225 mL of IPA and resulting gel was ground with 750 mL of IPA for further purification. The precipitate was collected by filtration and dried in vacuum oven at 45° C. for 24 h and at 55° C. for 2 days.

DSC of the dried sample showed a Tm of 138° C. with a ΔH of 29.6 J/g (1st heat) and Tg of 43° C. (2nd heat). Compression molding at 200° C. gave a film which gave a modulus of 93 ksi, ultimate tensile stress of 3.3 ksi, and an elongation at break of 460%.

Co-Polymers of Recurring Units of $I_2HBA-(CH_2)_n-I_2HBA$ with Recurring Units of PLLA, PCL and/or Other Groups.

As shown in the following examples, co-polymers may be prepared with other biocompatible recurring units, for example PLLA, PCL, PTMO, PTMC, poly(ethylene glycol) or combinations of those.

Example 9. Polymerization of ethane-1,2-diyl bis(4-hydroxy-3,5-diiodobenzoate) with PLLAdiol(7K) and PCLdiol(10K)

Into a 250 mL, 3-necked round bottomed flask were added 4.8 g (0.006 mol) of ethane-1,2-diyl bis(4-hydroxy-3,5-diiodobenzoate), 4.6 g of PLLAdiol(7K), 0.6 g of PCLdiol (10K), 54 mL of chloroform, and 2.1 g (0.027 mol) of pyridine and stirred under positive nitrogen pressure. To the flask was then added a solution of 0.72 g (0.0024 mol) of triphosgene in 24 mL of chloroform over 3 h using a syringe pump. The reaction mixture was not clear mainly due to poor solubility of ethane-1,2-diyl bis(4-hydroxy-3,5-diiodobenzoate). To the flask was added a mixture of 9.5 mL of THF and 0.5 mL of water to quench the reaction. This was followed by the addition of 75 mL of IPA. The precipitate was collected by filtration. To further purify the polymer it was stirred with 50 mL of DCM for 30 min. To the stirred suspension 75 mL IPA was added and the precipitate was further stirred with 250 mL acetone and then collected by filtration and dried in vacuum oven at 45° C. for 24 h and 55° C. for 2 days.

DSC of the dried sample showed a Tm of 146° C. with a ΔH of 9.6 J/g (1st) heat and Tg of 59.4° C. (2nd heat).

Example 10. Polymerization of hexane-1,6-diyl bis(4-hydroxy-3,5-diiodobenzoate) with PLLAdiol (7K) and PCLdiol(10K)

Into a 250 mL, 3-necked round bottomed flask were added 9.6 g (0.011 mol) of hexane-1,6-diyl bis(4-hydroxy-3,5-diiodobenzoate), 9.2 g of PLLAdiol(7K), 1.2 g of PCLdiol (10K), 54 mL of chloroform, and 4.2 g (0.053 mol) of pyridine and stirred under positive nitrogen pressure. To the flask was then added a solution of 1.37 g (0.005 mol) of triphosgene (TP) in 20 mL of chloroform over 3 h using a syringe pump. The reaction mixture was not clear mainly due to poor solubility of hexane-1,6-diylbis(4-hydroxy-3,5-diiodobenzoate). However, half through the addition of TP solution, the reaction mixture became clear. It remained clear till the end of the reaction. To the reaction mixture was added a mixture of 19 mL of THF and 1 mL of water to quench the reaction. This was followed by the addition of 150 mL of IPA with stirring and then allowed stratify. The supernatant was decanted out and the precipitate was stirred with 75 mL IPA. The precipitate was isolated by filtration and re-dissolved in 100 mL DCM. The solution was first precipitated with 150 mL of IPA and the precipitate was successively stirred with 75 mL IPA and then with 50 mL of IPA. The precipitate was collected by filtration and dried in vacuum oven at 45° C. for 24 h and 55° C. for 3 days.

DSC of the dried sample showed a Tm of 140° C. with a ΔH of 12.6 J/g (1st) heat and Tg of 59.7° C. (2nd heat). Compression molded film gave a modulus of 151 ksi, ultimate tensile stress of 6.6 ksi and an elongation at break of 225%.

It will be understood by those of skill in the art that numerous and various modifications can be made without departing from the spirit of the present invention. Therefore, it should be clearly understood that the various embodiments of the present invention described herein are illustrative only and not intended to limit the scope of the present invention.

What is claimed is:

1. A copolymer comprising a first repeating unit having the structure:

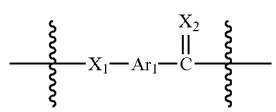

and a second repeating unit having the structure:

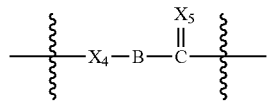

wherein $X_1$, $X_2$, $X_4$ and $X_5$, are independently selected from the group consisting of O, S and $NR_3$, wherein $R_3$ is selected from the group consisting of hydrogen and alkyl groups containing from one to six carbon atoms;
$Ar_1$ is phenylene substituted with at least one iodine atom, optionally further substituted with from one to three substituents independently selected from the group consisting of halogen, halomethyl, halomethoxy, methyl, methoxy, thiomethyl, nitro, sulfoxide and sulfonyl; and
B is selected from the group consisting of optionally substituted alkylene groups of 1 to 18 carbon atoms, optionally substituted heteroalkylene groups of 1 to 18 carbon atoms, optionally substituted alkenylene groups of 2 to 18 carbon atoms and optionally substituted heteroalkenylene groups of 2 to 18 carbon atoms;
wherein said copolymer is a block copolymer or a random copolymer or a graft copolymer.

2. The polymer of claim 1 wherein $X_1$, $X_2$, $X_4$ and $X_5$ are all oxygen atoms.

3. The polymer of claim 1 wherein $Ar_1$ is phenylene substituted with two iodine atoms in positions ortho to $X_1$.

4. The polymer of claim 1 wherein B is an alkylene group comprising the structure $(CH_2)_n$ wherein n is an integer from 1 to 10.

5. The polymer of claim 4 wherein n is an integer selected from the group consisting of 3, 5 and 6.

6. The polymer of claim 4 wherein B is a methylene group having the formula —$CH_2$—.

7. The polymer of claim 1 wherein B is a branched chain ethylene group having the formula —$CH(CH_3)$—.

8. A radio-opaque copolymer of lactic acid with 3,5-diiodo-4-hydroxybenzoic acid.

9. A radio-opaque copolymer of glycolic acid with 3,5-diiodo-4-hydroxybenzoic acid.

10. A radio-opaque copolymer of lactic acid and glycolic acid with 3,5-diiodo-4-hydroxybenzoic acid.

11. A compound having the structure:

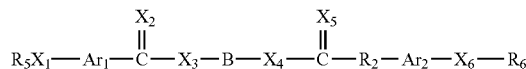

wherein $X_1$, $X_2$, $X_3$, $X_4$, $X_5$, and $X_6$ are independently selected from the group consisting of O, S and $NR_3$ wherein $R_3$ is selected from the group consisting of hydrogen and alkyl groups containing from one to six carbon atoms;
$Ar_1$ and $Ar_2$ are independently selected from the group consisting of phenylene,

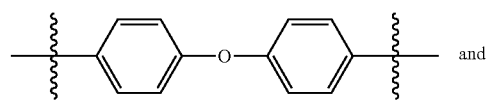 and

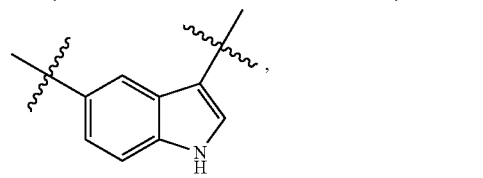

substituted with from one to four iodine atoms and optionally substituted with substituents independently selected from the group consisting of other halogens, halomethyl, halomethoxy, methyl, methoxy, thiomethyl, nitro, sulfoxide, and sulfonyl;
$R_2$ is a bond or is selected from the group consisting of optionally substituted alkylene containing from 1 to 10 carbon atoms, heteroalkylene containing from 1 to 10 carbon atoms, alkenylene containing from 2 to 10 carbon atoms, and heteroalkenylene containing from 2 to 10 carbon atoms;

$R_5$ and $R_6$ are independently selected from the group consisting of hydrogen and alkyl groups containing from one to six carbon atoms; and B is a carbonyl group.

12. The compound of claim 11 wherein each $X_1$, $X_2$, $X_3$, $X_4$, $X_5$ and $X_6$ is an O atom.

13. The compound of claim 12 wherein both $Ar_1$ and $Ar_2$ are phenylene groups substituted with two iodine atoms.

14. The compound of claim 11 wherein $R_2$ is an alkylene group containing from one to ten carbon atoms, or a bond.

15. The compound of claim 11 wherein $R_2$ is a bond.

16. A polymer comprising at least one repeating unit having the structure:

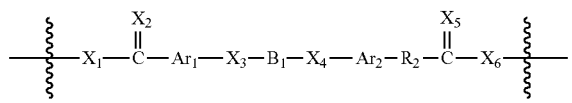

wherein, $X_1$, $X_2$, $X_3$, $X_4$, $X_5$, and $X_6$ are independently selected from the group consisting of O, S and $NR_3$ wherein $R_3$ is selected from the group consisting of hydrogen and alkyl groups containing from one to six carbon atoms;

$Ar_1$ and $Ar_2$ are independently selected from the group consisting of phenylene,

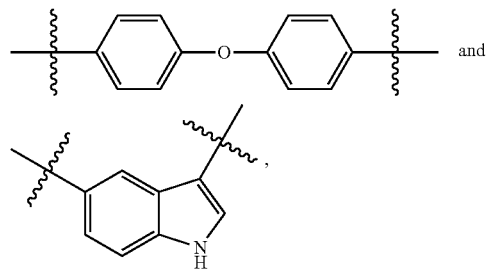

optionally substituted with from one to four substituents independently selected from the group consisting of halogen, halomethyl, halomethoxy, methyl, methoxy, thiomethyl, nitro, sulfoxide, and sulfonyl;

provided that at least one of $Ar_1$ and $Ar_2$ is substituted with at least one iodine atom;

$R_2$ is independently a bond or is selected from the group consisting of optionally substituted alkylene containing from 1 to 10 carbon atoms, heteroalkylene containing from 1 to 10 carbon atoms, alkenylene containing from 2 to 10 carbon atoms, and heteroalkenylene containing from 2 to 10 carbon atoms; and $B_1$ is a carbonyl group.

17. The polymer of claim 16 wherein each $X_1$, $X_2$, $X_3$, $X_4$, $X_5$, and $X_6$ is an oxygen atom.

18. The polymer of claim 16 wherein each $Ar_1$ and $Ar_2$ is independently phenylene substituted with at least one iodine atom.

19. The polymer of claim 18 wherein $Ar_1$ and $Ar_2$ are both phenylene groups substituted with two iodine atoms.

20. The polymer of claim 16 wherein $R_2$ is an alkylene group containing from one to ten carbon atoms, or a bond.

21. The polymer of claim 19 wherein $R_2$ is a bond.

22. The polymer of claim 16, characterized in that said polymer is a block copolymer with a hydroxy endcapped macromer, a mercapto endcapped macromer or an amino endcapped macro mer.

23. The polymer of claim 22, wherein said hydroxy endcapped macromer block comprises at least one macromer block selected from the group consisting of hydroxy endcapped polycaprolactones, hydroxy endcapped polylactic acids, hydroxy endcapped polyglycolic acids, hydroxy endcapped poly(lactic acid-co-glycolic acids), hydroxy endcapped poly(alkylene diols), poly(alkylene oxides) and hydroxy endcapped polydioxanones.

24. The polymer of claim 23, wherein the alkylene diol of said poly(alkylene diol) is hexane diol.

25. The polymer of claim 22, wherein the weight ratio of said polymer to said hydroxy-capped macromer is between about 25:75 and about 99:1.

26. The polymer of claim 16 comprising at least one repeating unit having the structure:

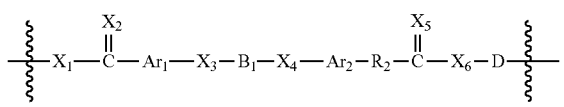

wherein the segment —$X_6$-D-$X_1$— is obtained from an intermediate $HX_6$-D-$X_1H$ which defines an alkylene diol containing up to 24 carbon atoms, an alkylene diamine containing up to 24 carbon atoms, an alkylene dimercaptan containing up to 24 carbon atoms, a hydroxy endcapped macromer, a mercapto endcapped macromer or an amine endcapped macromer.

27. The polymer of claim 26, wherein said hydroxy endcapped macromer block comprises at least one macromer block selected from the group consisting of hydroxy endcapped poly-caprolactones, hydroxy endcapped polylactic acids, hydroxy endcapped polyglycolic acids, hydroxy endcapped poly(lactic acid-co-glycolic acids), hydroxy endcapped poly(alkylene diols), poly(alkylene oxides) and hydroxy endcapped polydioxanones and hydroxyl endcapped poly(trimethylene carbonate).

28. A compound having the structure:

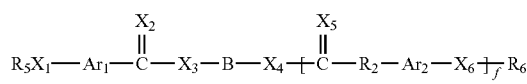

wherein, f is 0 or 1;

$X_1$, $X_2$, $X_3$, $X_4$, $X_5$, and $X_6$ are independently selected from the group consisting of O, S and $NR_3$ wherein $R_3$ is selected from the group consisting of hydrogen and alkyl groups containing from one to six carbon atoms;

$Ar_1$ and $Ar_2$ are independently selected from the group consisting of phenylene,

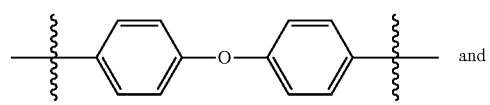

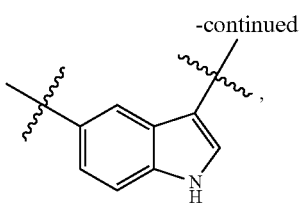

substituted with from one to four iodine atoms and optionally substituted with substituents independently selected from the group consisting of halogen, halomethyl, halomethoxy, methyl, methoxy, thiomethyl, nitro, sulfoxide, and sulfonyl;

$R_2$ is independently a bond or is selected from the group consisting of optionally substituted alkylene containing from 1 to 10 carbon atoms, heteroalkylene containing from 1 to 10 carbon atoms, alkenylene containing from 2 to 10 carbon atoms, and heteroalkenylene containing from 2 to 10 carbon atoms;

$R_5$ and $R_6$ are independently selected from the group consisting of hydrogen and alkyl groups containing from one to six carbon atoms; and B is selected from the group consisting of an optionally substituted alkylene groups of 1 to 18 carbon atoms and groups having the structure:

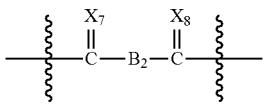

wherein $B_2$ is selected from the group consisting of optionally substituted alkylene, optionally substituted heteroalkylene, optionally substituted alkenylene and optionally substituted heteroalkenylene, or $B_2$, $X_3$, $X_4$, $X_7$ and $X_8$ are selected so that the segment

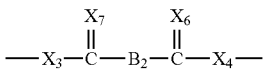

is obtained from an intermediate

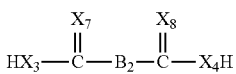

which defines an endcapped macromer.

29. The compound of claim 28 wherein said endcapped macromer is a macromer dicarboxylate.

30. The compound of claim 29 wherein each $X_1$, $X_2$, $X_3$, $X_4$, $X_5$, and $X_6$ is an oxygen atom.

31. The compound of claim 30 wherein both $Ar_1$ and $Ar_2$ are phenylene groups substituted with two iodine atoms.

32. The compound of claim 31 wherein $R_2$ is an alkylene group containing from one to ten carbon atoms or a bond.

33. The compound of claim 31 wherein $R_2$ is a bond.

34. The compound of claim 33 wherein B is an alkylene group containing 1 to 18 carbon atoms.

35. The compound of claim 34 wherein B is an alkylene group containing 3, 5 or 6 carbon atoms.

36. The compound of claim 29 wherein said macromer dicarboxylate comprises a polylactic acid macromer block.

37. The compound of claim 29 wherein said macromer dicarboxylate comprises a polyglycolic acid macromer block.

38. The compound of claim 29, wherein said macromer dicarboxylate comprises a poly(lactic acid-co-glycolic acid) macromer block.

39. The compound of claim 29 wherein said macromer dicarboxylate comprises a polycaprolactone macromer block.

40. The compound of claim 29, wherein said macromer dicarboxylate comprises a macromer block selected from the group consisting of poly(alkylene diols), poly(alkylene oxides) and polydioxanones.

41. The compound of claim 40, wherein the alkylene diol of said poly(alkylene diol) is hexane diol.

42. A polymer comprising at least one repeating unit having the structure:

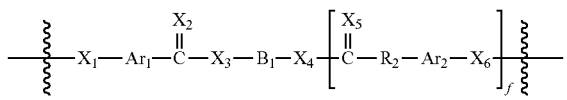

wherein, f is 0 or 1;

$X_1$, $X_2$, $X_3$, $X_4$, $X_5$, and $X_6$ are independently selected from the group consisting of O, S and $NR_3$ wherein $R_3$ is selected from the group consisting of hydrogen and alkyl groups containing from one to six carbon atoms;

$Ar_1$ and $Ar_2$ are independently selected from the group consisting of phenylene, substituted with from one to four iodine atoms and optionally further independently substituted with substituents independently selected from the group consisting of halogen, halomethyl, halomethoxy, methyl, methoxy, thiomethyl, nitro, sulfoxide, and sulfonyl;

$R_2$ is a bond or is selected from the group consisting of optionally substituted alkylene containing from 1 to 10 carbon atoms, heteroalkylene containing from 1 to 10 carbon atoms, alkenylene containing from 2 to 10 carbon atoms, and heteroalkenylene containing from 2 to 10 carbon atoms; and $B_1$ is selected from the group consisting of an optionally substituted alkylene groups of 1 to 18 carbon atoms and groups having the structure:

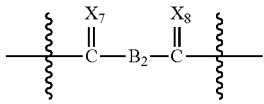

wherein $B_2$ is selected from the group consisting of optionally substituted alkylene, optionally substituted heteroalkylene, optionally substituted alkenylene and optionally substituted heteroalkenylene, or $B_2$, $X_3$, $X_4$, $X_7$ and $X_8$ are selected so that the segment

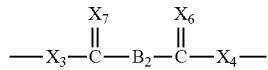

is obtained from an intermediate

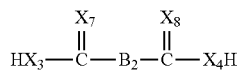

which defines a capped macromer structure.

43. The polymer of claim 42, wherein said capped macromer structure is a macromer dicarboxylate.

44. The polymer of claim 42 wherein each $X_1$, $X_2$, $X_3$, $X_4$, $X_5$, and $X_6$ is an O atom.

45. The polymer of claim 44 wherein $Ar_1$ and $Ar_2$ are both phenylene.

46. The polymer of claim 45 wherein both phenylene groups are substituted with two iodine atoms.

47. The polymer of claim 42 wherein $R_2$ is an alkylene group containing from one to ten carbon atoms, or a bond.

48. The polymer of claim 47 wherein $R_2$ is a bond.

49. The polymer of claim 42 wherein $B_1$ is an alkylene group containing 1 to 18 carbon atoms.

50. The polymer of claim 49 wherein $B_1$ is an alkylene group containing 3, 5 or 6 carbon atoms.

51. The polymer of claim 43 wherein said macromer dicarboxylate comprises a polylactic acid macromer block.

52. The polymer of claim 43 wherein said macromer dicarboxylate comprises a polyglycolic acid macromer block.

53. The polymer of claim 43 wherein said macromer dicarboxylate comprises a poly(lactic acid-co-glycolic acid) macromer block.

54. The polymer of claim 43 wherein said macromer dicarboxylate comprises a polycaprolactone macromer block.

55. The polymer of claim 43, wherein said macromer dicarboxylate comprises at least one macromer block selected from the group consisting of hydroxy end-capped poly(alkylene diols), poly(alkylene oxides) and hydroxy endcapped polydioxanones.

56. The polymer of claim 55, wherein the alkylene diol of said poly(alkylene diol) is hexane diol.

57. The polymer of claim 42, characterized in that said polymer is a block copolymer with a hydroxy endcapped macromer, a mercapto endcapped macromer or an amine endcapped macromer.

58. The polymer of claim 57 wherein said hydroxy endcapped macromer block comprises at least one macromer block selected from the group consisting of hydroxy endcapped polycaprolactones, hydroxy endcapped polylactic acids, hydroxy endcapped polyglycolic acids, hydroxy endcapped poly(lactic acid-co-glycolic acids), hydroxy endcapped poly(alkylene diols), poly(alkylene oxides) and hydroxy endcapped polydioxanones.

59. The polymer of claim 58, wherein the alkylene diol of said poly(alkylene diol) is hexane diol.

60. The polymer of claim 58, wherein the weight ratio of said polymer to said hydroxy-capped macromer is between about 25:75 and about 99:1.

61. The polymer of claim 42 comprising at least one repeating unit having the structure:

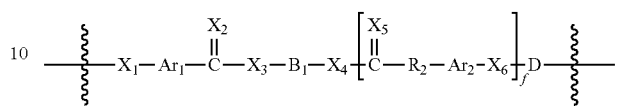

wherein D is selected from the group consisting of

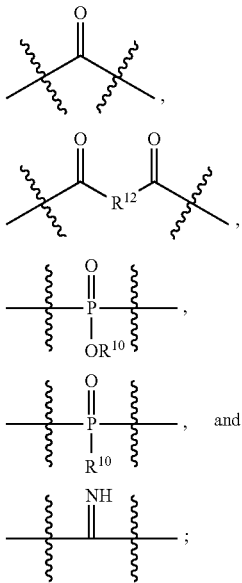

wherein $R_{10}$ is selected from the group consisting of H, saturated and unsaturated, substituted and unsubstituted alkyl, heteroalkyl, alkenyl and heteroalkenyl groups containing from one to 18 carbon atoms, and $R_{12}$ is selected from the group consisting of saturated and unsaturated, substituted and unsubstituted alkylene containing from 1 to 10 carbon atoms, heteroalkylene containing from 1 to 10 carbon atoms, alkenylene containing from 2 to 10 carbon atoms, and heteroalkenylene containing from 2 to 18 carbon atoms and alkylarylene, heteroalkylarylene, alkenylarylene and heteroalkenylarylene groups containing up to 12 carbon atoms.

62. The polymer of claim 61 wherein D is a carbonyl group having the following structure:

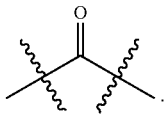 [SMILES: *C(*)=O]

63. The polymer of claim 61 wherein D is a group having the structure:

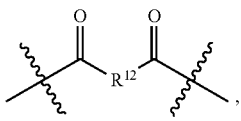

wherein R$_{12}$ is selected from the group consisting of alkylene containing from 1 to 18 carbon atoms, heteroalkylene containing from 1 to 18 carbon atoms, alkenylene containing from 2 to 18 carbon atoms, and heteroalkenylene containing from 2 to 18 carbon atoms.

64. The polymer of claim 63 wherein R$_{12}$ is a heteroalkylene group having up to 16 carbon atoms.

65. The polymer of claim 64 wherein R$_{12}$ has two or four carbon atoms.

66. A compound comprising the structure:

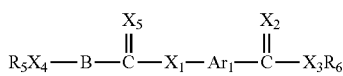

wherein X$_1$, X$_2$, X$_3$, X$_4$ and X$_5$, are independently selected from the group consisting of O, S and NR$_3$ wherein R$_3$ is selected from the group consisting of hydrogen and alkyl groups containing from one to six carbon atoms;

Ar$_1$ is selected from the group consisting of

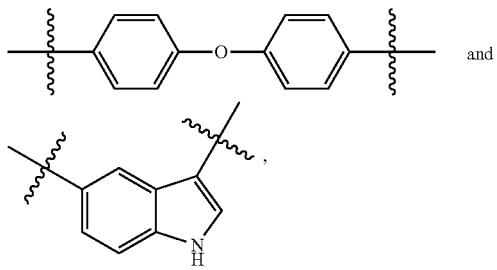

optionally substituted with from one to four substituents independently selected from the group consisting of halogen, halomethyl, halomethoxy, methyl, methoxy, thiomethyl, nitro, sulfoxide, and sulfonyl;

or Ar$_1$ is phenylene substituted with from 1 to 4 halogen atoms;

R$_5$ and R$_6$ are independently selected from the group consisting of hydrogen and alkyl groups containing from one to six carbon atoms; and B is selected from the group consisting of optionally substituted alkylene groups of 1 to 18 carbons, optionally substituted heteroalkylene groups of 1 to 18 carbons, optionally substituted alkenylene groups of 2 to 18 carbons and optionally substituted heteroalkenylene groups of 2 to 18 carbons.

67. The compound of claim 66 wherein X$_1$, X$_2$, X$_3$, X$_4$ and X$_5$ are all oxygen atoms.

68. The compound of claim 66 wherein Ar$_1$ is phenylene substituted with two iodine atoms in positions ortho to X$_1$.

69. The compound of claim 66 wherein B is a methylene group having the formula —CH$_2$—.

70. The compound of claim 66 wherein B is a branched chain ethylene group having the formula —CH(CH$_3$)—.

71. A polyester consisting essentially of monomer units independently selected from the group consisting of the structure:

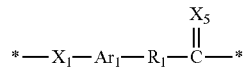

wherein X$_1$ and X$_5$, are independently selected from the group consisting of O, S and NR$_3$, R$_3$ is selected from the group consisting of hydrogen and alkyl groups containing from one to six carbon atoms;

Ar$_1$ is selected from the group consisting of

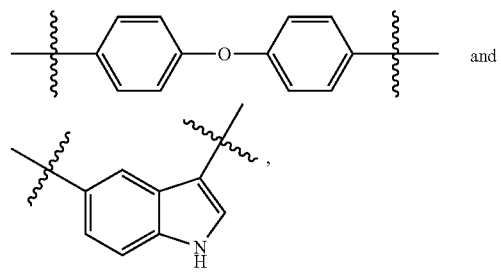

optionally substituted with from one to four substituents independently selected from the group consisting of halogen, halomethyl, halomethoxy, methyl, methoxy, thiomethyl, nitro, sulfoxide and sulfonyl;

or Ar$_1$ is phenylene substituted with from 1 to 4 iodine atoms;

and each R$_1$ is independently a bond or is selected from the group consisting of optionally substituted alkylene containing from 1 to 10 carbon atoms, heteroalkylene containing from 1 to 10 carbon atoms, alkenylene containing from 2 to 10 carbon atoms, and heteroalkenylene containing from 2 to 10 carbon atoms, wherein at least one R$_1$ is a bond.

72. The polyester of claim 71 consisting essentially of monomer units independently selected from the group consisting of the structure:

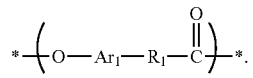

73. The polyester of claim 71 wherein Ar$_1$ is a phenylene substituted with at least one iodine atom.

74. The polyester of claim 73 wherein Ar$_1$ is phenylene substituted with two iodine atoms in positions ortho to X$_1$.

75. The polyester of claim 71 wherein R$_1$ is an alkylene group containing from one to ten carbon atoms or a bond.

76. The polymer of claim 75 wherein R$_1$ is a bond.

77. A polymer comprising at least one repeating unit having the structure:

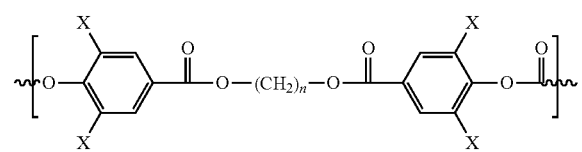

wherein n is an integer from 1 to 18; and wherein each X is independently H or I, provided that at least one X is I, and further comprising at least one repeating unit having the structure of PLLA, PCL, PTMO, PTMC, poly(ethylene glycol), or combinations thereof.

78. The polymer of claim 77 wherein at least two of the X are I.

79. The polymer of claim 77 wherein each X is I, and the at least one repeating unit has the structure:

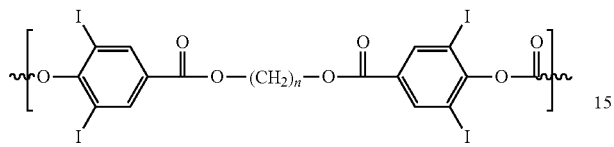

wherein n is an integer from 1 to 18, and further comprising at least one repeating unit having the structure of PLLA, PCL, PTMO, PTMC, poly(ethylene glycol), or combinations thereof.

80. The polymer of claim 79, wherein n is an integer from 1 to 6.

81. The polymer of claim 79, comprising one or more repeating units having structure(s) selected from the group consisting of PLLA, PCL and combinations thereof.

* * * * *